United States Patent
Köhler et al.

(10) Patent No.: US 10,039,282 B2
(45) Date of Patent: Aug. 7, 2018

(54) SIX-MEMBERED C—N-BONDED ARYL SULPHIDE AND ARYL SULPHOXIDE DERIVATIVES AS PESTICIDES

(71) Applicant: BAYER CROPSCIENCE AKTIENGESELLSCHAFT, Monheim am Rhein (DE)

(72) Inventors: Adeline Köhler, Langenfeld (DE); Silvia Cerezo-Galvez, Langenfeld (DE); Bernd Alig, Königswinter (DE); Reiner Fischer, Monheim (DE); Johanna Julia Hahn, Düsseldorf (DE); Kerstin Ilg, Köln (DE); Daniela Portz, Vettweiβ (DE); Olga Malsam, Rösrath (DE); Peter Lösel, Leverkusen (DE); David Wilcke, Düsseldorf (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/104,004

(22) PCT Filed: Dec. 12, 2014

(86) PCT No.: PCT/EP2014/077576
§ 371 (c)(1),
(2) Date: Jun. 13, 2016

(87) PCT Pub. No.: WO2015/091267
PCT Pub. Date: Jun. 25, 2015

(65) Prior Publication Data
US 2016/0316751 A1    Nov. 3, 2016

(30) Foreign Application Priority Data
Dec. 16, 2013    (EP) ..................... 13197460

(51) Int. Cl.
*A01N 43/54*    (2006.01)
*C07D 239/36*    (2006.01)
*A01N 43/707*    (2006.01)

(52) U.S. Cl.
CPC .......... *A01N 43/54* (2013.01); *A01N 43/707* (2013.01); *C07D 239/36* (2013.01)

(58) Field of Classification Search
CPC .............................. A01N 43/54; C07D 239/36
See application file for complete search history.

(56) References Cited

U.S. PATENT DOCUMENTS

| | | | |
|---|---|---|---|
| 6,509,354 B1 * | 1/2003 | Toriyabe | A01N 31/08 514/222.2 |
| 2003/0069242 A1 | 4/2003 | Toriyabe et al. | |

FOREIGN PATENT DOCUMENTS

| | | |
|---|---|---|
| WO | 1999/055668 A1 | 11/1999 |
| WO | 2010/100189 A1 | 9/2010 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
International Search Report dated Feb. 19, 2015, issued in PCT/EP2014/077576, English translation thereof.

* cited by examiner

*Primary Examiner* — Kendra D Carter
(74) *Attorney, Agent, or Firm* — McBee Moore Woodward & Vanik IP, LLC

(57) ABSTRACT

Illustrated are compounds of the formula (I), which are suitable for controlling animal pests including arthropods and in particular insects and acarids

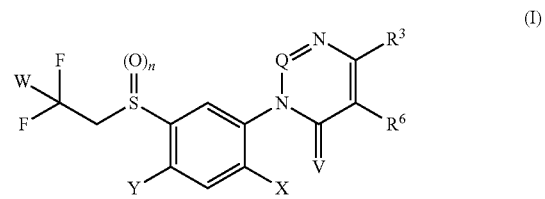

in which the structural elements have the meanings given in the description.

15 Claims, No Drawings

SIX-MEMBERED C—N-BONDED ARYL SULPHIDE AND ARYL SULPHOXIDE DERIVATIVES AS PESTICIDES

CROSS REFERENCE TO RELATED APPLICATIONS

This application is a § 371 National Stage Application of PCT/EP2014/077576, filed 12 Dec. 2014, which claims priority to 13197460.2, filed 16 Dec. 2013.

BACKGROUND

Field of the Invention

The present application relates to novel heterocyclic compounds, to processes for preparation thereof and to the use thereof for controlling animal pests, which include arthropods and especially insects.

Description of Related Art

Aryl sulphide and aryl sulphoxide derivatives and their insecticidal and acaricidal action are already known, for example from WO 1999/055668 A1. Arylquinazolinones and their insecticidal and acaricidal action are already known from WO 2010/100189 A1.

Crop protection agents, which also include pesticides, have to meet many demands, for example in relation to efficacy, persistence, and spectrum of action and possible use. Questions of toxicity and of combinability with other active compounds or formulation auxiliaries play a role, as does the question of the expense that the synthesis of an active compound requires. In addition, resistances can occur. For all these reasons, the search for novel crop protection compositions cannot be considered to be complete, and there is a constant need for novel compounds having properties which, compared to the known compounds, are improved at least in relation to individual aspects.

SUMMARY

It was an object of the present invention to provide compounds which widen or improve the spectrum of the pesticides in various respects.

This object, and further objects which are not stated explicitly but can be discerned or derived from the connections discussed herein, are achieved by novel compounds of the formula (I)

$$\text{(I)}$$

in which (Embodiment 1-1)
V represents oxygen or represents sulphur or represents substituted nitrogen;
Q represents substituted carbon or represents nitrogen;
$R^3$ and $R^6$ independently of one another represent
hydrogen, halogen, cyano or nitro; or
represent alkyl, alkenyl, alkynyl, alkoxy, alkylsulphanyl, alkylsulphinyl, alkylsulphonyl, haloalkylcarbonyl, alkylcarbonyl or alkoxycarbonyl, where the radicals mentioned above may optionally be substituted; or
represent cycloalkyl, cycloalkylalkyl or cycloalkenyl in which the rings may contain at least one heteroatom selected from the group consisting of sulphur, oxygen and nitrogen, with the proviso that two oxygen atoms must not be directly adjacent to one another, where the radicals mentioned above may optionally be substituted; or
represent aryl, heteroaryl, arylalkyl or heteroarylalkyl, where the radicals mentioned above may optionally be substituted; or
represent NR'R",
where R' and R" independently of one another represent hydrogen, cyano, alkyl, haloalkyl, cyanoalkyl, hydroxyalkyl, alkoxyalkyl, alkylsulphanylalkyl, alkylsulphinylalkyl, alkysulphonylalkyl, alkenyl, haloalkenyl, cyanoalkenyl, alkynyl, haloalkynyl, cyanoalkynyl, acyl or alkoxycarbonyl;
or
where R' and R" together with the nitrogen atom to which they are attached may form an optionally substituted, saturated or unsaturated three- to eight-membered ring optionally interrupted by one or more heteroatoms independently selected from the group consisting of O, S and N, with the proviso that two oxygen atoms must not be directly adjacent to one another; or
W represents hydrogen or halogen;
n represents the number 0, 1 or 2;
Y represents hydrogen, halogen, $(C_1-C_6)$-alkyl, trifluoromethyl, $(C_2-C_6)$-haloalkyl, $(C_1-C_6)$-alkoxy, $(C_1-C_6)$-haloalkoxy or amino; or
represents NR'''R'''',
where R''' and R'''' independently of one another represent hydrogen, $(C_1-C_6)$-alkyl or $(C_2-C_6)$-haloalkyl;
X represents hydrogen, halogen, cyano, $(C_1-C_6)$-alkyl, $(C_1-C_6)$-haloalkyl or $(C_1-C_6)$-alkoxy.

DETAILED DESCRIPTION OF A PREFERRED EMBODIMENT

It has been additionally found that the novel compounds of the formula (I) have good efficacy as pesticides, for example against arthropods and especially insects, nematodes and acarids, and additionally generally have very good compatibility with plants, especially crop plants, and/or have favourable toxicological and/or environmentally relevant properties.

Preferred substituents or ranges for the radicals shown in the compounds of the formula (I) are illustrated below (Embodiment 2-1).
V represents oxygen;
Q represents C—$R^5$ or nitrogen, where
$R^5$ represents hydrogen, halogen, amino, cyano, nitro, $(C_1-C_6)$-alkyl, $(C_1-C_6)$-haloalkyl, $(C_1-C_6)$-alkylsulphanyl, $(C_1-C_6)$-alkylsulphinyl, $(C_1-C_6)$-alkylsulphonyl, $(C_1-C_6)$-haloalkylsulphanyl, $(C_1-C_6)$-haloalkylsulphinyl, $(C_1-C_6)$-haloalkylsulphonyl, $(C_3-C_6)$-cycloalkyl or $(C_1-C_6)$-alkoxy;
$R^3$ and $R^6$ independently of one another
represent hydrogen, halogen, cyano or nitro; or
represent $(C_1-C_6)$-alkyl, $(C_1-C_6)$-haloalkyl, $(C_2-C_6)$-alkenyl, $(C_2-C_6)$-alkynyl, $(C_1-C_6)$-alkoxy, $(C_1-C_6)$-haloalkoxy, $(C_1-C_6)$-haloalkylsulphanyl, $(C_1-C_6)$-haloalkylsulphinyl, $(C_1-C_6)$-haloalkylsulphonyl, $(C_1-C_6)$-alkylsulphanyl, $(C_1-C_6)$-alkylsulphinyl, $(C_1-C_6)$- alkylsulphonyl, (C$_1$-C$_5$)-alkylcarbonyl, (C$_1$-C$_5$)-haloalkylcarbonyl or (C$_2$-C$_6$)-alkoxy carbonyl; or represent (C$_3$-C$_6$)-cycloalkyl, (C$_3$-C$_6$)-cycloalkyl-(C$_1$-C$_3$)-alkyl or (C$_3$-C$_6$)-cycloalkenyl, where the radicals mentioned above may optionally be substituted by halogen, alkyl, cyano, nitro, alkoxy, haloalkyl or haloalkoxy; or represent phenyl, heteroaryl, phenyl-(C$_1$-C$_3$)-alkyl or heteroaryl-(C$_1$-C$_3$)-alkyl, where the radicals mentioned above may optionally be substituted by halogen, alkyl, cyano, nitro, alkoxy, haloalkyl or haloalkoxy; or represent NR'R",
where R' and R" independently of one another represent hydrogen, cyano, (C$_1$-C$_4$)-alkyl, (C$_1$-C$_4$)-haloalkyl, (C$_1$-C$_4$)-cyanoalkyl, (C$_1$-C$_4$)-hydroxyalkyl, (C$_1$-C$_4$)-alkoxy, (C$_1$-C$_4$)-alkyl, (C$_1$-C$_4$)-alkylsulphanyl-(C$_1$-C$_4$)-alkyl, (C$_1$-C$_4$)-alkylsulphinyl-(C$_1$-C$_4$)-alkyl, (C$_1$-C$_4$)-alkylsulphonyl-(C$_1$-C$_4$)-alkyl, (C$_3$-C$_4$)-alkenyl, (C$_3$-C$_4$)-haloalkenyl, (C$_2$-C$_4$)-cyanoalkenyl, (C$_3$-C$_4$)-alkynyl, (C$_3$-C$_4$)-haloalkynyl, (C$_3$-C$_4$)-cyanoalkynyl, (C$_1$-C$_4$)-alkylcarbonyl or (C$_1$-C$_4$)-alkoxy carbonyl;
or
where R' and R" together with the nitrogen atom to which they are attached may form an optionally halogen-, alkyl-, cyano-, nitro-, alkoxy-, haloalkyl- or haloalkoxy-substituted, saturated or unsaturated three- to eight-membered ring optionally interrupted by one or more heteroatoms independently selected from the group consisting of O, S and N, with the proviso that two oxygen atoms must not be directly adjacent to one another; or W represents hydrogen or halogen;
n represents the number 0 or 1;
Y represents hydrogen, halogen, (C$_1$-C$_4$)-alkyl, trifluoromethyl, (C$_2$-C$_4$)-haloalkyl, (C$_1$-C$_4$)-alkoxy, (C$_1$-C$_4$)-haloalkoxy or amino; or
represents NR'''R'''',
where R''' and R'''' independently of one another represent hydrogen, (C$_1$-C$_4$)-alkyl or (C$_2$-C$_4$)-haloalkyl;
X represents hydrogen, halogen, cyano, (C$_1$-C$_4$)-alkyl, (C$_1$-C$_4$)-haloalkyl or (C$_1$-C$_4$)-alkoxy.

In a further embodiment (Embodiment 2-2), the preferred substituents or ranges of the radicals given in the compounds of the formula (I) are as follows:
V represents oxygen;
Q represents C—R$^5$ or nitrogen, where
R$^5$ represents hydrogen, halogen, amino, cyano, nitro, (C$_1$-C$_6$)-alkyl, (C$_1$-C$_6$)-haloalkyl, (C$_1$-C$_6$)-alkylsulphanyl, (C$_1$-C$_6$)-alkylsulphinyl, (C$_1$-C$_6$)-alkylsulphonyl, (C$_1$-C$_6$)-haloalkylsulphanyl, (C$_1$-C$_6$)-haloalkylsulphinyl, (C$_1$-C$_6$)-haloalkylsulphonyl or (C$_1$-C$_6$)-alkoxy;
R$^3$ and R$^6$ independently of one another
represent hydrogen, halogen, cyano or nitro; or
represent (C$_1$-C$_6$)-alkyl, (C$_1$-C$_6$)-haloalkyl, (C$_2$-C$_6$)-alkenyl, (C$_2$-C$_6$)-alkynyl, (C$_1$-C$_6$)-alkoxy, (C$_1$-C$_6$)-haloalkoxy, (C$_1$-C$_6$)-haloalkylsulphanyl, (C$_1$-C$_6$)-haloalkylsulphinyl, (C$_1$-C$_6$)-haloalkylsulphonyl, (C$_1$-C$_6$)-alkylsulphanyl, (C$_1$-C$_6$)-alkylsulphinyl, (C$_1$-C$_6$)-alkylsulphonyl, (C$_1$-C$_5$)-haloalkylcarbonyl or (C$_2$-C$_6$)-alkoxycarbonyl; or represent NR'R",
where R' and R" independently of one another represent hydrogen, cyano, (C$_1$-C$_4$)-alkyl, (C$_1$-C$_4$)-haloalkyl, (C$_1$-C$_4$)-cyanoalkyl, (C$_1$-C$_4$)-hydroxyalkyl, (C$_1$-C$_4$)-alkoxy, (C$_1$-C$_4$)-alkyl, (C$_1$-C$_4$)-alkylsulphanyl-(C$_1$-C$_4$)-alkyl, (C$_1$-C$_4$)-alkylsulphinyl-(C$_1$-C$_4$)-alkyl, (C$_1$-C$_4$)-alkylsulphonyl-(C$_1$-C$_4$)-alkyl, (C$_3$-C$_4$)-alkenyl, (C$_3$-C$_4$)-haloalkenyl, (C$_2$-C$_4$)-cyanoalkenyl, (C$_3$-C$_4$)-alkynyl, (C$_3$-C$_4$)-haloalkynyl, (C$_3$-C$_4$)-cyanoalkynyl, (C$_1$-C$_4$)-alkylcarbonyl or (C$_1$-C$_4$)-alkoxycarbonyl;

W represents hydrogen or halogen;
n represents the number 0 or 1;
Y represents hydrogen, halogen, (C$_1$-C$_4$)-alkyl, trifluoromethyl, (C$_2$-C$_4$)-haloalkyl, (C$_1$-C$_4$)-alkoxy, (C$_1$-C$_4$)-haloalkoxy or amino; or
represents NR'''R'''',
where R''' and R'''' independently of one another represent hydrogen, (C$_1$-C$_4$)-alkyl or (C$_2$-C$_4$)-haloalkyl;
X represents hydrogen, halogen, cyano, (C$_1$-C$_4$)-alkyl, (C$_1$-C$_4$)-haloalkyl or (C$_1$-C$_4$)-alkoxy.

In a further embodiment (Embodiment 2-3), the preferred substituents or ranges of the radicals given in the compounds of the formula (I) are as follows:
V represents oxygen;
Q represents C—R$^5$ or nitrogen, where
R$^5$ represents hydrogen, halogen, amino, cyano, nitro, (C$_1$-C$_6$)-alkyl, (C$_1$-C$_6$)-haloalkyl, (C$_1$-C$_6$)-alkylsulphanyl, (C$_1$-C$_6$)-alkylsulphinyl, (C$_1$-C$_6$)-alkylsulphonyl, (C$_1$-C$_6$)-haloalkylsulphanyl, (C$_1$-C$_6$)-haloalkylsulphinyl, (C$_1$-C$_6$)-haloalkylsulphonyl, (C$_3$-C$_6$)-cycloalkyl or (C$_1$-C$_6$)-alkoxy;
R$^3$ and R$^6$ independently of one another
represent (C$_1$-C$_5$)-alkylcarbonyl; or
represent (C$_3$-C$_6$)-cycloalkyl, (C$_3$-C$_6$)-cycloalkyl-(C$_1$-C$_3$)-alkyl or (C$_3$-C$_6$)-cycloalkenyl, where the radicals mentioned above may optionally be substituted by halogen, alkyl, cyano, nitro, alkoxy, haloalkyl or haloalkoxy; or represent phenyl, heteroaryl, phenyl-(C$_1$-C$_3$)-alkyl or heteroaryl-(C$_1$-C$_3$)-alkyl, where the radicals mentioned above may optionally be substituted by halogen, alkyl, cyano, nitro, alkoxy, haloalkyl or haloalkoxy; or
represent NR'R",
where R' and R" together with the nitrogen atom to which they are attached may form an optionally halogen-, alkyl-, cyano-, nitro-, alkoxy-, haloalkyl- or haloalkoxy-substituted, saturated or unsaturated three- to eight-membered ring optionally interrupted by one or more heteroatoms independently selected from the group consisting of O, S and N, with the proviso that two oxygen atoms must not be directly adjacent to one another; or W represents hydrogen or halogen;
n represents the number 0 or 1;
Y represents hydrogen, halogen, (C$_1$-C$_4$)-alkyl, trifluoromethyl, (C$_2$-C$_4$)-haloalkyl, (C$_1$-C$_4$)-alkoxy, (C$_1$-C$_4$)-haloalkoxy or amino; or
represents NR'''R'''',
where R''' and R'''' independently of one another represent hydrogen, (C$_1$-C$_4$)-alkyl or (C$_2$-C$_4$)-haloalkyl;
X represents hydrogen, halogen, cyano, (C$_1$-C$_4$)-haloalkyl or (C$_1$-C$_4$)-alkoxy.

More preferred substituents or ranges for the radicals shown in the compounds of the formula (I) are illustrated below (Embodiment 3-1).
V represents oxygen;
Q represents C—R$^5$ or nitrogen, where
R$^5$ represents hydrogen, halogen, amino, cyano, nitro, (C$_1$-C$_4$)-alkyl, (C$_1$-C$_4$)-haloalkyl, (C$_3$-C$_6$)-cycloalkyl or (C$_1$-C$_4$)-alkoxy;
R$^3$ and R$^6$ independently of one another
represent hydrogen or halogen; or
represent (C$_1$-C$_4$)-alkyl, (C$_1$-C$_4$)-haloalkyl, (C$_1$-C$_4$)-alkoxy or (C$_1$-C$_4$)-haloalkoxy; or represent $(C_3-C_6)$-cycloalkyl or $(C_3-C_6)$-cycloalkyl-$(C_1-C_2)$-alkyl, where all of the radicals mentioned above may optionally be substituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or represent phenyl or phenyl-$(C_1-C_3)$-alkyl, where the radicals mentioned above may optionally be mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or represent heteroaryl selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, indolyl, isoindolyl and indazolyl, where the radicals mentioned above may optionally be mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or represent NR'R",
where R' and R" independently of one another represent hydrogen, $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-alkylsulphanyl-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl, $(C_1-C_4)$-alkylcarbonyl or $(C_1-C_4)$-alkoxycarbonyl;
or
where R' and R" together with the nitrogen atom to which they are attached may form a saturated four- to six-membered ring which is optionally mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy and optionally interrupted by a heteroatom selected from the group consisting of O, S and N;

W represents hydrogen or fluorine;
n represents the number 0 or 1;
Y represents hydrogen, fluorine, chlorine, bromine, methyl, ethyl, trifluoromethyl, methoxy, ethoxy, difluoromethoxy, trifluoromethoxy, amino, methylamino or dimethylamino;
X represents hydrogen, fluorine, chlorine, bromine, cyano, methyl, ethyl, trifluoromethyl, methoxy or ethoxy.

In a further embodiment (Embodiment 3-2), the more preferred substituents or ranges of the radicals given in the compounds of the formula (I) are as follows:
V represents oxygen;
Q represents C—$R^5$ or nitrogen, where
$R^5$ represents hydrogen, halogen, amino, cyano, nitro, $(C_1-C_4)$-alkyl, $(C_1-C_4)$-haloalkyl, $(C_3-C_6)$-cycloalkyl or $(C_1-C_4)$-alkoxy;
$R^3$ and $R^6$ independently of one another
represent hydrogen or halogen; or
represent $(C_1-C_4)$-alkyl, $(C_1-C_4)$-haloalkyl, $(C_1-C_4)$-alkoxy or $(C_1-C_4)$-haloalkoxy; or
represent NR'R",
where R' and R" independently of one another represent hydrogen, $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-alkylsulphanyl-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl, $(C_1-C_4)$-alkylcarbonyl or $(C_1-C_4)$-alkoxycarbonyl;

W represents hydrogen or fluorine;
n represents the number 0 or 1;
Y represents hydrogen, fluorine, chlorine, bromine, methyl, ethyl, trifluoromethyl, methoxy, ethoxy, difluoromethoxy, trifluoromethoxy, amino, methylamino or dimethylamino;
X represents hydrogen, fluorine, chlorine, bromine, cyano, methyl, ethyl, trifluoromethyl, methoxy or ethoxy.

In a further embodiment (Embodiment 3-3), the more preferred substituents or ranges of the radicals given in the compounds of the formula (I) are as follows:
V represents oxygen;
Q represents C—$R^5$ or nitrogen, where
$R^5$ represents hydrogen, halogen, amino, cyano, nitro, $(C_1-C_4)$-alkyl, $(C_1-C_4)$-haloalkyl, $(C_3-C_6)$-cycloalkyl or $(C_1-C_4)$-alkoxy;
$R^3$ and $R^6$ independently of one another
represent $(C_3-C_6)$-cycloalkyl or $(C_3-C_6)$-cycloalkyl-$(C_1-C_2)$-alkyl, where the radicals mentioned above may optionally be substituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or
represent phenyl or phenyl-$(C_1-C_3)$-alkyl, where the radicals mentioned above may optionally be mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or
represent heteroaryl selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, indolyl, isoindolyl and indazolyl, where the radicals mentioned above may optionally be mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or
represent NR'R",
where R' and R" together with the nitrogen atom to which they are attached may form a saturated four- to six-membered ring which is optionally mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy and optionally interrupted by a heteroatom selected from the group consisting of O, S and N;

W represents hydrogen or fluorine;
n represents the number 0 or 1;
Y represents hydrogen, fluorine, chlorine, bromine, methyl, ethyl, trifluoromethyl, methoxy, ethoxy, difluoromethoxy, trifluoromethoxy, amino, methylamino or dimethylamino;
X represents hydrogen, fluorine, chlorine, bromine, cyano, methyl, ethyl, trifluoromethyl, methoxy or ethoxy.

Particularly preferred substituents or ranges for the radicals shown in the compounds of the formula (I) are illustrated below (Embodiment 4-1).
V represents oxygen;
Q represents C—$R^5$, where
$R^5$ represents hydrogen, methyl, ethyl, methoxy, cyclopropyl or trifluoromethyl;
$R^3$ and $R^6$ independently of one another represent hydrogen, methyl, ethyl, trifluoromethyl, difluoromethyl, difluorochloromethyl, cyclopropyl or phenyl;
W represents hydrogen or fluorine;
n represents the number 0 or 1;

Y represents fluorine, chlorine, bromine, methyl, trifluoromethyl or methoxy;
X represents hydrogen, chlorine, fluorine or methyl;
where X and Y represent in particular the following combinations (Y,X): (Me,F), (Me,H), (Me,Cl), (Me, Me), (Cl,Cl), (Cl,F), (MeO,F), (MeO,H), (Cl,H), (Br, H), (Br,F), (F,F), (CF$_3$,H), (CF$_3$,F).

In a further embodiment (Embodiment 4-2), the particularly preferred substituents or ranges of the radicals given in the compounds of the formula (I) are as follows:
V represents oxygen;
Q represents C—R$^5$, where
R$^5$ represents hydrogen, methyl, ethyl or trifluoromethyl;
R$^3$ and R$^6$ independently of one another represent hydrogen, methyl, ethyl, trifluoromethyl, difluoromethyl;
W represents hydrogen or fluorine;
n represents the number 0 or 1;
Y represents fluorine, chlorine, bromine, methyl, trifluoromethyl or methoxy;
where X and Y represent in particular the following combinations (Y,X): (Me,F), (Me,H), (Me,Cl), (Me, Me), (Cl,Cl), (Cl,F), (MeO,F), (MeO,H), (Cl,H), (Br, H), (Br,F), (F,F), (CF$_3$,H), (CF$_3$,F).

In a further embodiment (Embodiment 4-3), the particularly preferred substituents or ranges of the radicals given in the compounds of the formula (I) are as follows:
V represents oxygen;
Q represents C—R$^5$, where
R$^5$ represents hydrogen, methyl, ethyl, methoxy, cyclopropyl or trifluoromethyl;
R$^3$ and R$^6$ independently of one another represent difluorochloromethyl, cyclopropyl or phenyl;
W represents hydrogen or fluorine;
n represents the number 0 or 1;
Y represents fluorine, chlorine, bromine, methyl, trifluoromethyl or methoxy;
X represents hydrogen, chlorine, fluorine or methyl;
where X and Y represent in particular the following combinations (Y,X): (Me,F), (Me,H), (Me,Cl), (Me, Me), (Cl,Cl), (Cl,F), (MeO,F), (MeO,H), (Cl,H), (Br, H), (Br,F), (F,F), (CF$_3$,H), (CF$_3$,F).

In a further embodiment (Embodiment 4-4), the particularly preferred substituents or ranges of the radicals given in the compounds of the formula (I) are as follows:
V represents oxygen;
Q represents C—R$^5$, where
R$^5$ represents hydrogen, methyl, ethyl, methoxy, cyclopropyl or trifluoromethyl;
R$^3$ and R$^6$ independently of one another represent hydrogen, fluorine, methyl, ethyl, isopropyl, trifluoromethyl, pentafluoroethyl, difluoromethyl, 1,1-difluoroethyl, difluorochloromethyl, cyclopropyl or phenyl;
W represents hydrogen or fluorine;
n represents the number 0 or 1;
Y represents fluorine, chlorine, bromine, methyl, trifluoromethyl or methoxy;
X represents hydrogen, chlorine, fluorine or methyl;
where X and Y represent in particular the following combinations (Y,X): (Me,F), (Me,H), (Me,Cl), (Me, Me), (Cl,Cl), (Cl,F), (MeO,F), (MeO,H), (Cl,H), (Br, H), (Br,F), (F,F), (CF$_3$,H), (CF$_3$,F).

In a further embodiment (Embodiment 4-5), the particularly preferred substituents or ranges of the radicals given in the compounds of the formula (I) are as follows:
V represents oxygen;
Q represents C—R$^5$, where
R$^5$ represents hydrogen, methyl, ethyl, methoxy, cyclopropyl or trifluoromethyl;
R$^3$ and R$^6$ independently of one another represent fluorine, isopropyl, pentafluoroethyl, 1,1-difluoroethyl, difluorochloromethyl, cyclopropyl or phenyl;
W represents hydrogen or fluorine;
n represents the number 0 or 1;
Y represents fluorine, chlorine, bromine, methyl, trifluoromethyl or methoxy;
X represents hydrogen, chlorine, fluorine or methyl;
where X and Y represent in particular the following combinations (Y,X): (Me,F), (Me,H), (Me,Cl), (Me, Me), (Cl,Cl), (Cl,F), (MeO,F), (MeO,H), (Cl,H), (Br, H), (Br,F), (F,F), (CF$_3$,H), (CF$_3$,F).

Very particularly preferred substituents or ranges for the radicals shown in the compounds of the formula (I) are illustrated below (Embodiment 5-1).
V represents oxygen;
Q represents C—R$^5$, where
R$^5$ represents hydrogen;
R$^3$ represents trifluoromethyl;
R$^6$ represents hydrogen;
represents fluorine;
n represents the number 0 or 1;
Y represents chlorine or methyl;
X represents chlorine, fluorine or methyl;
where X and Y represent in particular the following combinations (Y,X): (Me,F), (Me,Me), (Cl,Cl).

In a further embodiment (Embodiment 5-2), the very particularly preferred substituents or ranges of the radicals given in the compounds of the formula (I) are as follows:
V represents oxygen;
represents C—R$^5$, where
R$^5$ represents hydrogen or methyl;
R$^3$ represents hydrogen, methyl, ethyl, cyclopropyl, isopropyl, difluoromethyl, trifluoromethyl, pentafluoroethyl, 1,1-difluoroethyl or phenyl;
R$^6$ represents hydrogen, fluorine or methyl;
W represents fluorine;
n represents the number 0 or 1;
Y represents bromine, chlorine or methyl;
X represents hydrogen, chlorine, fluorine or methyl;
where X and Y represent in particular the following combinations (Y,X): (Me,H), (Me,Cl), (Me,F), (Me, Me), (Cl,Cl), (Cl,F), (Cl,H), (Br,F).

When sulphur and/or nitrogen occur in rings in the above definitions, for example in expressions such as "in which the rings may contain at least one heteroatom from the group of sulphur, oxygen (where oxygen atoms must not be directly adjacent) and nitrogen" or "in which one or two ring members may each be replaced by a heteroatom from the group of sulphur, oxygen (where oxygen atoms must not be directly adjacent) and nitrogen", unless stated otherwise, the sulphur may also be present in the form of SO or SO$_2$; the nitrogen, if it is not in the form of —N=, as well as NH, may also be in the form of N-alkyl (especially N—C$_1$-C$_6$-alkyl).

In the broadest and the preferred definitions, unless stated otherwise,
halogen is selected from the group of fluorine, chlorine, bromine and iodine, preferably in turn from the group of fluorine, chlorine and bromine,
hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3, 4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the further preferred definitions, unless stated otherwise,
halogen is selected from the group of fluorine, chlorine, bromine and iodine, preferably in turn from the group of fluorine, chlorine and bromine,
Halogen-substituted radicals, for example haloalkyl, are mono- or polyhalogenated up to the maximum possible number of substituents. In the case of polyhalogenation, the halogen atoms can be identical or different. Halogen is fluorine, chlorine, bromine and iodine, especially fluorine, chlorine and bromine.

Saturated or unsaturated hydrocarbon radicals, such as alkyl or alkenyl, may each be straight-chain or branched if possible, including in combination with heteroatoms, as, for example, in alkoxy.

Optionally substituted radicals may be mono- or polysubstituted, where the substituents in the case of polysubstitution may be the same or different. If substituents are intended or optionally intended, the substitutents are, unless indicated otherwise, halogen, alkyl, cycloalkyl, cyano, nitro, alkoxy, haloalkyl or haloalkoxy, in particular fluorine, chlorine, $(C_1-C_3)$-alkyl, $(C_3-C_6)$-cycloalkyl (in particular cyclopropyl), cyano, $(C_1-C_3)$-alkoxy, $(C_1-C_3)$-haloalkyl or $(C_1-C_3)$-haloalkoxy.

The radical definitions or elucidations given above in general terms or within preferred ranges apply correspondingly to the end products (including the compounds of the formula (I) with the substructure (I-A), which will be elucidated later), and to the starting materials and intermediates. These radical definitions can be combined with one another as desired, i.e. including combinations between the respective preferred ranges.

Preference is given in accordance with the invention to compounds of the formula (I) in which a combination of the definitions given above as preferred is present, and every embodiment described above as preferred constitutes an independent combination, in particular a combination as described in Embodiment 2-1 or in Embodiment 2-2 or in Embodiment 2-3.

More preference is given in accordance with the invention to compounds of the formula (I) in which a combination of the definitions given above as more preferred is present, and every embodiment described above as more preferred constitutes an independent combination, in particular a combination as described in Embodiment 3-1 or in Embodiment 3-2 or in Embodiment 3-3.

Particular preference is given in accordance with the invention to compounds of the formula (I) in which a combination of the definitions given above as particularly preferred is present, and every embodiment described above as particularly preferred constitutes an independent combination, in particular a combination as described in Embodiment 4-1 or in Embodiment 4-2 or in Embodiment 4-3 or in Embodiment 4-4 or in Embodiment 4-5.

Very particular preference is given in accordance with the invention to compounds of the formula (I) in which a combination of the definitions given above as very particularly preferred is present, and every embodiment described above as very particularly preferred constitutes an independent combination, in particular a combination as described in Embodiment 5-1 or in Embodiment 5-2.

In further preferred embodiments, the invention relates to compounds of the formula (I) in which Q represents C—$R^5$. This results in compounds of the formula (I-A)

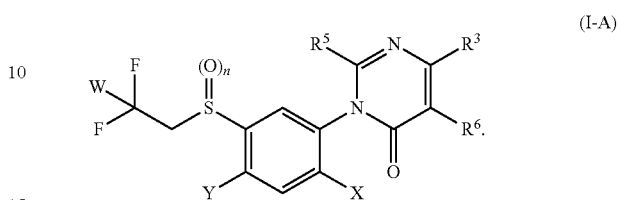

(I-A)

In the compounds of the formula (I) defined by the structure (I-A), the radicals or structural elements $R^5$, $R^3$, $R^6$, W, n, Y and X have the meanings described above, in particular as described in Embodiment 1-1.

More particularly, X and Y represent the following (Y,X) combinations: (Me,F), (Me,H), (Me,Cl), (Me,Me), (Cl,Cl), (Cl,F), (MeO,F), (MeO,H), (Cl,H), (Br,H), (Br,F), (F,F), ($CF_3$,H), ($CF_3$,F), particular preference being given to the following (Y,X) combinations: (Me,F), (Me,Me), (Cl,Cl).

Preferred from among the compounds of the formula (I) defined by structure (I-A) are those compounds in which a combination of the meanings given above as preferred is present, and every embodiment described above as preferred constitutes an independent combination, in particular a combination as described in Embodiment 2-1 or in Embodiment 2-2 or in Embodiment 2-3.

More preferred from among the compounds of the formula (I) defined by structure (I-A) are those compounds in which a combination of the meanings given above as more preferred is present, and every embodiment described above as more preferred constitutes an independent combination, in particular a combination as described in Embodiment 3-1 or in Embodiment 3-2 or in Embodiment 3-3.

Particularly preferred from among the compounds of the formula (I) defined by structure (I-A) are those compounds in which a combination of the meanings given above as particularly preferred is present, and every embodiment described above as particularly preferred constitutes an independent combination, in particular a combination as described in Embodiment 4-1 or in Embodiment 4-2 or in Embodiment 4-3 or in Embodiment 4-4 or in Embodiment 4-5.

Very particularly preferred from among the compounds of the formula (I) defined by structure (I-A) are those compounds in which a combination of the meanings given above as very particularly preferred is present, and every embodiment described above as very particularly preferred constitutes an independent combination, in particular a combination as described in Embodiment 5-1 or in Embodiment 5-2.

The compounds of the formula (I) can also be present as salts, in particular acid addition salts and metal salt complexes. The compounds of the formula (I) and the acid addition salts and metal salt complexes thereof have good efficacy, especially for controlling animal pests, which include arthropods and in particular insects and acarids.

Suitable salts of the compounds of the general formula (I) include customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulphates, trihydrosulphates, or phosphates, salts with organic carboxylic acids or sulphonic acids, for example formates, acetates, trifluoroacetates, maleates, tartrates, methanesulphonates, benzenesulphonates or para-toluenesulphonates, salts with basic amino acids, for example arginates, aspartates or glutamates, and the like.

The compounds of the formula (I) may possibly also, depending on the nature of the substituents, be in the form of stereoisomers, i.e. in the form of geometric and/or optically active isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof for controlling animal pests, including arthropods and especially insects and acarids. An individual configuration of the invention is therefore directed to the presence of the R enantiomer, or to a mixture comprising a majority of the R enantiomer, preferably where the ratio of R to S enantiomer is at least 60:40 and, with increasing preference, at least 70:30, 75:25, 80:20, 85:15 and 90:10. A further individual configuration of the invention is therefore directed to the presence of the S enantiomer, or to a mixture comprising a majority of the S enantiomer, preferably where the ratio of S to R enantiomer is at least 60:40 and, with increasing preference, at least 70:30, 75:25, 80:20, 85:15 and 90:10.

The compounds of the formula (I) may be present in different polymorphic forms or as a mixture of different polymorphic forms. Both the pure polymorphs and the polymorph mixtures form part of the subject-matter of the invention and can be used in accordance with the invention.

The compounds according to the invention are defined in general terms by the formula (I), which includes all the possible rotamers and mixtures thereof.

The compounds of the formula (I) according to the invention can be prepared by customary methods known to those skilled in the art. Various preparation processes, which also form part of the subject-matter of the invention, are described below.

Preparation Processes

The compounds of the general formula (I) can be classified into compounds where n=0 (Ia), n=1 (Ib) and n=2 (Ic) and can be prepared according to the scheme below, for example according to Methods A and B, as described in the application WO 2010/100189. In deviation from these methods, the compounds of the formula (I) can also be prepared by Processes D and E or the Processes F and G illustrated below, or by processes described in WO1999/055668.

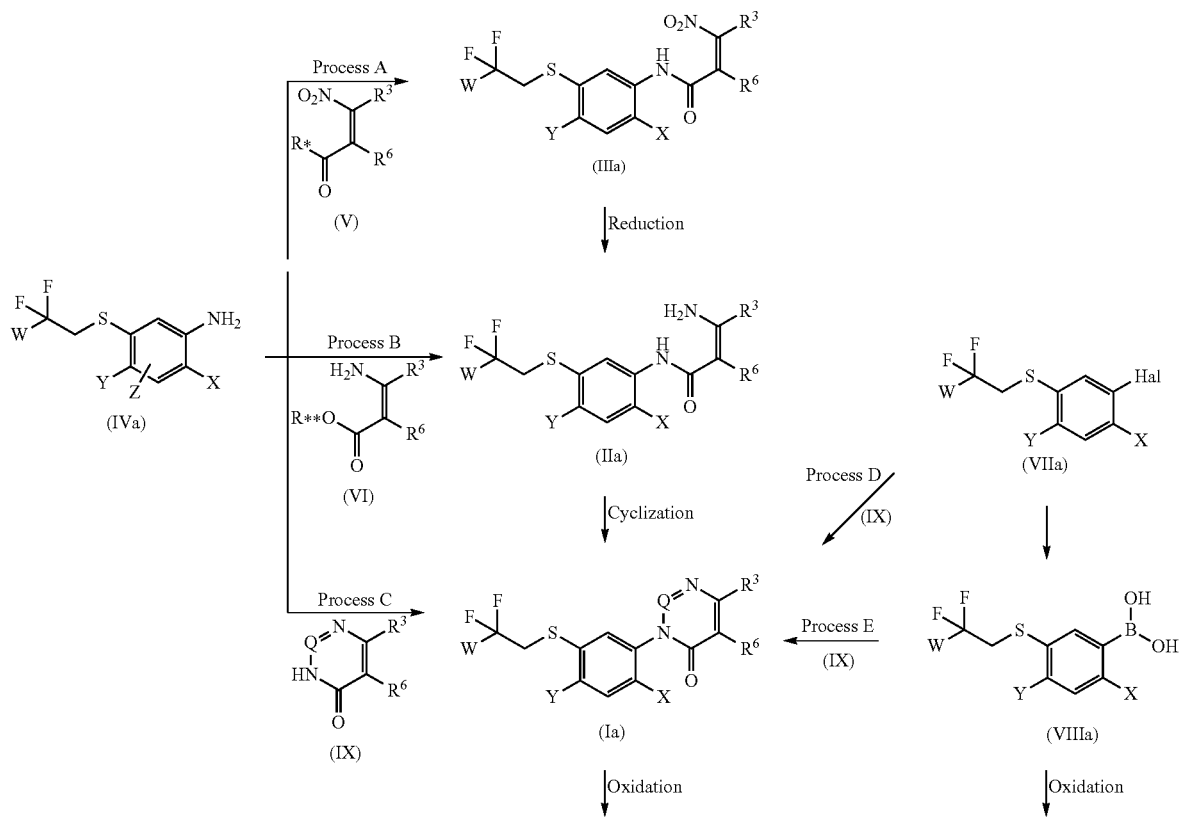

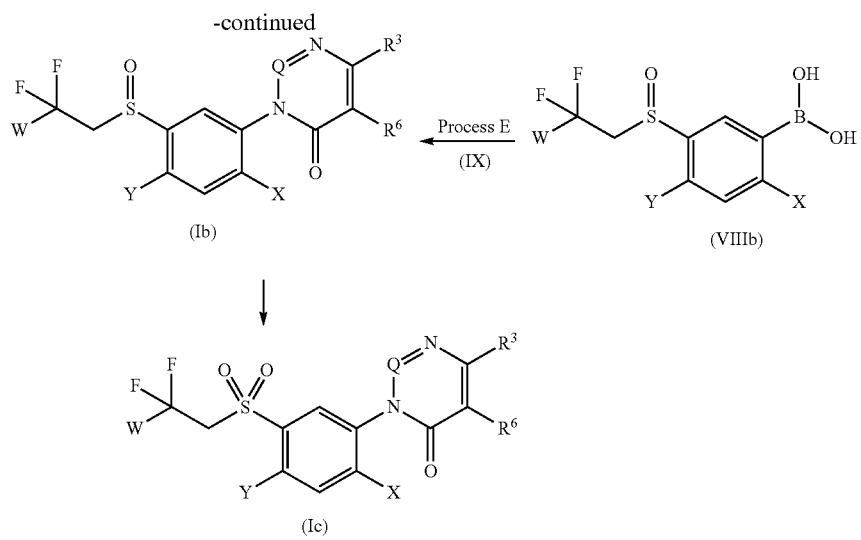

Process A

Compounds of the formula (Ma) or tautomers thereof can be prepared, for example, according to Process A by reacting anilines of the formula (IVa) with nitro compounds of the formula (V) in which R* represents hydroxy or halogen (preferably Cl and Br).

Many different methods for preparing carboxamides from carboxylic acids (R*=hydroxy) or carbonyl halides (R=halogen) are known, for example G. Benz in Comprehensive Organic Synthesis, $1^{st}$ Ed., Pergamon Press, Oxford, 1991, Vol. 6, pp. 381-417; P. D. Bailey et al. in Comprehensive Organic Functional Group Transformation, 1st Ed., Elsevier Science Ltd., Oxford, 1995, Vol. 5, pp. 257-308 and R. C. Larock in Comprehensive Organic Transformations, 2nd Ed., Wiley-VCH, New York, Weinheim, 1999, pp. 1929-1994. Carbonyl chlorides can be isolated or used as generated in situ.

The amidation reactions are optionally carried out in the presence of a condensing agent, optionally in the presence of an acid activator, optionally in the presence of an acid acceptor and optionally in the presence of a solvent. Useful condensing agents are all the condensing agents typically usable for such amidation reactions. Examples which may be mentioned are acid halide formers such as phosgene, phosphorus trichloride, oxalyl chloride or thionyl chloride; carbodiimides such as N,N'-dicyclohexylcarbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methoiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU) and 1-hydroxybenzotriazole. These reagents can be used separately or, if appropriate, in combination. Useful acid acceptors are all customary inorganic or organic bases, for example triethylamine, diisopropylethylamine, N-methylmorpholine or N,N-dimethylaminopyridine. Process A according to the invention is optionally carried out in the presence of a suitable reaction auxiliary, for example N,N-dimethylformamide or N,N-dimethylaminopyridine.

Furthermore, it is also possible to use mixed anhydrides for preparing (Ma), as published, for example, in J. Am. Chem. Soc 1967, 5012. In this process, it is possible to use various chloroformic esters, for example isobutyl chloroformate, isopropyl chloroformate. It is likewise possible for this purpose to use diethylacetyl chloride, trimethylacetyl chloride and the like.

Compounds of the general formula (IIa) or tautomers thereof can be prepared, for example, by reduction of the nitro compounds of the general formula (Ma) according to methods known from the literature. Suitable processes for such reductions are in particular metal-mediated reactions such as, for example, tin(II) chloride, iron powder, zinc powder, Raney nickel, palladium(0) on carbon or platinum dioxide (as hydrate). The metal-mediated reductions, for example with tin(II) chloride, can be carried out according to a process described in Organic Syntheses Coll. Vol. (III), 453.

Process B

Alternatively, compounds of the general formula (IIa) can be prepared by an acylation reaction according to Process B where an aniline of the general formula (IVa) is reacted with a suitable carboxylic acid derivative of the formula (VI), where R** preferably represents alkyl. This can take place without activation, as described by B. M. Trost and I. Fleming in Comprehensive Organic Synthesis, Ed. Pergamon, 1991, Vol. 6. Alternatively, the literature discloses activation methods by formation of an aluminium amide, as by T. Ooi and K. Marouka in Science of Synthesis, Ed. Georg Thieme, 2003, Vol. 7, 225-246. These aluminium amides can be obtained from the anilines or their salts by reaction with trimethylaluminium or their air-stable adduct with 1,4-diazobicyclo[2.2.3]octane (DABCO), as described by S. Woodward in Tet. Lett. 2006, 47, 5767-5769.

R** may also represent hydrogen, so that all synthesis methods described in Process A would also be suitable for the synthesis of compounds of the formula (IIa).

Various methods are suitable for the preparation of thioethers of the general formula (Ia). Examples which may be mentioned are: starting with compounds of the formula (IIa) by ring closure; starting with anilines of the formula (IVa) by reaction with compounds of the formula (IX) according to Process C or starting with halides of the formula (VIIa) or boronic acids of the formula (VIIIa) or (VIIIb) by metal-catalysed reactions according to Process D or Process E.

Cyclization

For Q=C—$R^5$, where $R^5$ represents H or alkyl, the preparation of the thioether of the general formula (Ia) can take place according to methods known from the literature by cyclization of open-chain precursors of the formula (IIa) with an orthoester such as triethyl orthoformate or triethyl orthoacetate, optionally in the presence of a solvent and diluent, optionally in the presence of an acid of organic nature (such as para-toluenesulphonic acid) or inorganic nature (such as hydrochloric acid or sulphuric acid) in catalytic or stoichiometric amounts or in excess or instead of the solvent or diluent. Alternatively, the thioether of the general formula (Ia) can be prepared by methods known from the literature by reaction with DMF-DMA and subsequent reaction with formic acid.

For Q=C—$R^5$, where $R^5$ represents alkyl or haloalkyl, the preparation of the thioether of the general formula (Ia) can also be carried out by reaction with the appropriate carboxylic anhydrides or acid chlorides according to methods known from the literature, for example as described for $R^5$=$CF_3$ in the patent WO 2008/039489.

For Q=N, the compounds of the formula (Ia) can be prepared by diazotization of the compounds of the formula (IIa) according to methods known from the literature. For example, a nitrite source such as sodium nitrite or isobutyl nitrite is added to compounds of the formula (IIa), typically in water, alcohol or a polar inert solvent, at from 0 to 5° C. in the presence of an organic or inorganic acid. Exemplary reaction conditions can be found, for example, in the patent WO 2004/242572 or in J. Amer. Chem. Soc. Perkin Trans. 1, 1980, 633-638.

Process C

Alternatively, the compounds of the formula (Ia) can be prepared from anilines of the formula (IVa) by reaction with compounds of the formula (IX) or their tautomeric hydroxypyrimidinones according to Process C. As described by Yang et al. in Org. Lett. 2009, 11, 6, 1421-1424, the N-arylation of the hydroxypyrimidinones is carried out under mild reaction conditions, for example by HATU-mediated coupling with primary amines using DBU as base in acetonitrile as solvent, in most cases at room temperature or at up to 70° C.

Process D

An alternative preparation of the compounds of the formula (Ia) is provided by the reaction of halides of the formula (VIIa) with compounds of the formula (IX) under metal-catalysed reaction conditions. The literature discloses numerous methods, for example in Chem. Pharm. Bull. 1997, 45, 4, 719-721; in Tet. Lett. 2006, 47, 7677-7680; or Synlett 2008, 9, 1335-1340, where the metal source used is copper iodide in the presence of a base and optionally a ligand at elevated temperatures (for example from 120 to 150° C.).

Process E

It has likewise been found that the reaction of boronic acids of the formula (VIIIa) with compounds of the formula (IX) by metal-catalysed reactions may serve to prepare the compounds of the formula (Ia). An overview of such reactions can be found in Synthesis 2011, 6, 829-856. A suitable metal source is copper(II) acetate, as in Synlett 2010, 5, 721-724; Tetrahedron 2006, 62, 8, 1764-1771; Tetrahedron Lett. 2005, 46, 34, 5699-5702 or WO 2010/104818.

The oxidation of the boronic acids of the formula (VIIIa) or their boronic esters according to methods known from the literature, for example with sodium periodate, leads to sulphoxides of the formula (VIIIb) which can likewise be reacted with compounds of the formula (IX) under metal-catalysed reaction conditions, resulting in the target compounds (Ib).

When carrying out the Processes D and E according to the invention, any commercial microwave apparatus suitable for these reactions may optionally be employed (for example Anton Paar Monowave 300, CEM Discover S, Biotage Initiator 60).

Alternatively, compounds of the general formula (Ib) may be prepared by methods similar to those mentioned here carried out in a different order, for example by oxidation of the anilines of the formula (IVa) to give sulphoxides of the formula (IVb) and their further conversion according to Process A, B or C.

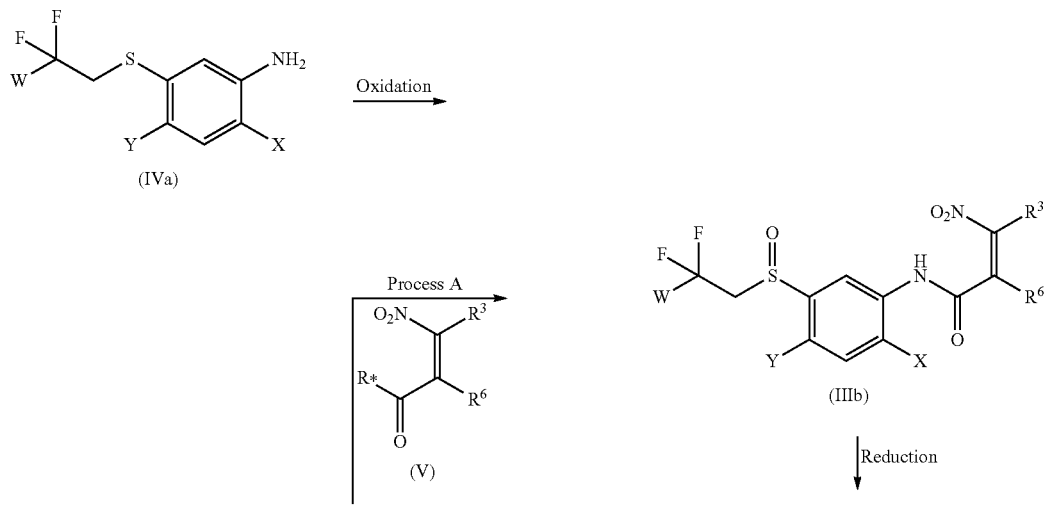

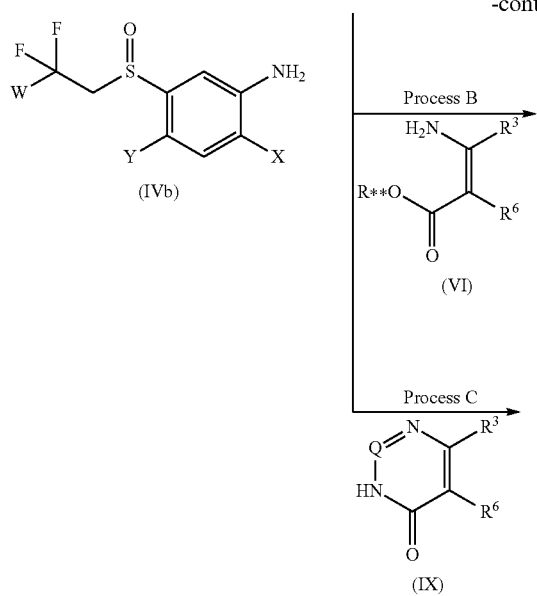
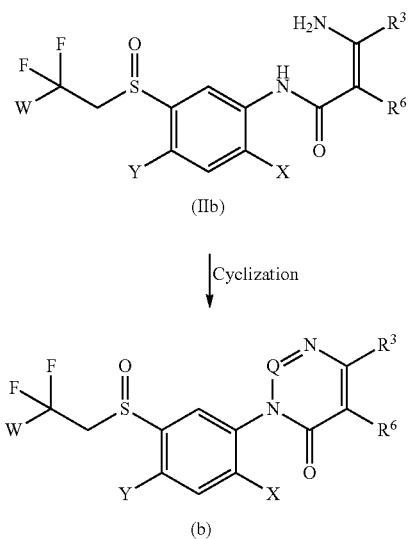

In deviation from these methods, the compounds of the formula (I) where Q=C—R⁵ can also be prepared according to Process F.

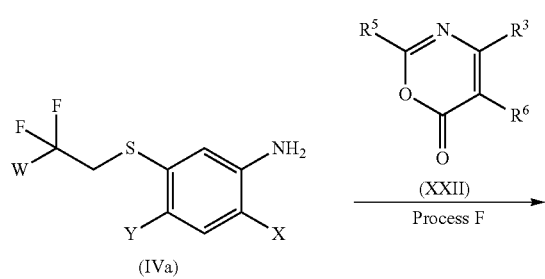

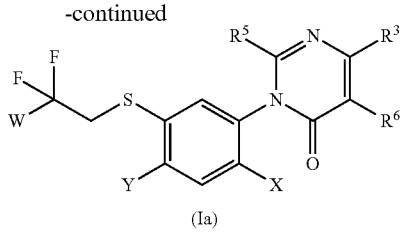

Anilines of the formula (IVa) can be reacted with oxazinones of the formula (XXII) to give target compounds of the formula (Ia), for example according to Assiut Univ. J. of Chemistry 2006, 45-63. Oxazinones of the formula (XXII) are known or can be prepared by methods known from the literature, for example as in Journal of the Chemical Society 1965, 4240-4246.

In deviation from these methods, the compounds of the formula (I) can also be prepared according to Process G.

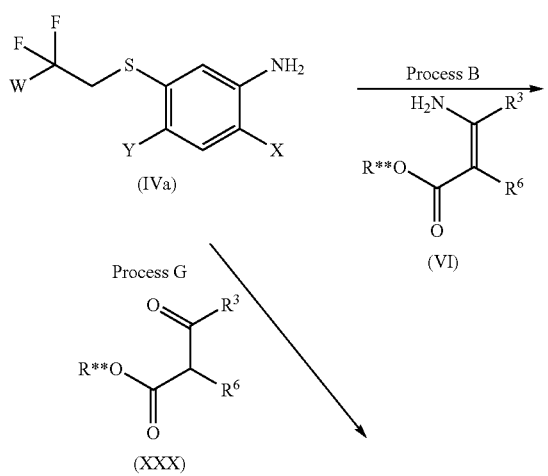
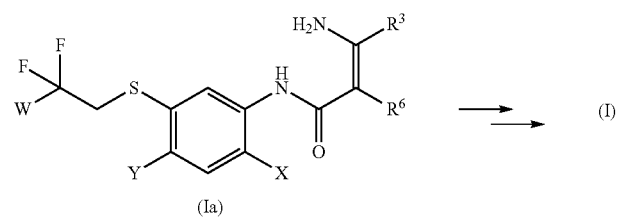

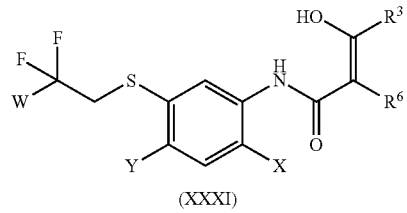

(XXXI)

Anilines of the formula (IVa) can be reacted with β-keto esters of the formula (XXX) to give enols of the formula (XXXI), for example according to WO 2004/056785. The amination of the enols of the formula (XXXI) with an aminating agent such as ammoniak or ammonium acetate affords the open-chain compound of the formula (IIa). The preparation of the compounds of the formula (I) from (IIa) has already been described above.

Reactions in the Microwave

In the performance of the processes according to the invention, it is optionally possible to use any commercial microwave apparatus suitable for these reactions (e.g. Anton Paar Monowave 300, CEM Discover S, Biotage Initiator 60).

Thionation

A further general process for preparing the compounds of the general formula (Ia) or (Ib) according to the invention in which V is sulphur involves the conversion of the carbonyl in corresponding precursors to the thiocarbonyl group with the aid of suitable thionating reagents, for example phosphorus pentasulphide or Lawesson's reagent in a suitable solvent, for example pyridine, xylene or cumene. This variant is described in numerous publications, for example in J. Amer. Chem. Soc. 1956, 1938-1941, Chem. Pharm. Bull. 1962, 10, 647-652, U.S. Pat. No. 3,007,927, DE 2554866 or WO 2000026194.

General Preparation Processes for Oxidizing Thioethers to Sulphoxides

Compounds of the general formula (Ib) can be prepared through oxidation by processes known from the literature from compounds of the general formula (Ia), for example by means of an oxidizing agent in a suitable solvent and diluent. Suitable oxidizing agents are, for example, dilute nitric acid, hydrogen peroxide and peroxycarboxylic acids, for example meta-chloroperbenzoic acid. Suitable solvents are inert organic solvents, typically acetonitrile and halogenated solvents such as dichloromethane, chloroform or dichloroethane.

A large number of different methods are suitable for generating enantiomerically enriched sulphoxides, as described by A. R. Maguire in ARKIVOC, 2011(i), 1-110: metal-catalysed asymmetric oxidations of thioethers, for example with titanium or vanadium as the most frequently employed catalyst sources, in the form of Ti(O$^i$Pr$_4$) or VO(acac)$_2$, together with a chiral ligand and an oxidizing agent such as tert-butyl hydroperoxide (TBHP), 2-phenylpropan-2-yl hydroperoxide (CHP) or hydrogen peroxide; non-metal-catalysed asymmetric oxidations employing chiral oxidizing agents or chiral catalysts; electrochemical or biological asymmetric oxidations and also kinetic resolution of sulphoxides and nucleophilic shift (according to Andersen's method).

The enantiomers can also be obtained from the racemate, for example by separating them on a preparative scale by chiral HPLC.

Description of the Starting Materials and Intermediates

Anilines of the formula (IV), halides of the formula (VII) and boronic acids of the formula (VIII) are central building blocks for preparing the compounds of the formula (I).

The anilines of the general formula (IV) can be classified into compounds where n=0 (IVa) and n=1 (IVb).

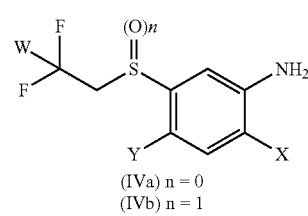

(IVa) n = 0
(IVb) n = 1

Anilines of the formula (IVa) are known from the literature, for example from JP 2007/284356, or they can be synthesized by processes known from the literature.

The anilines of the general formula (IVa) can be prepared, for example, as in the scheme below;

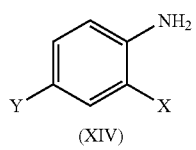

(XIV)

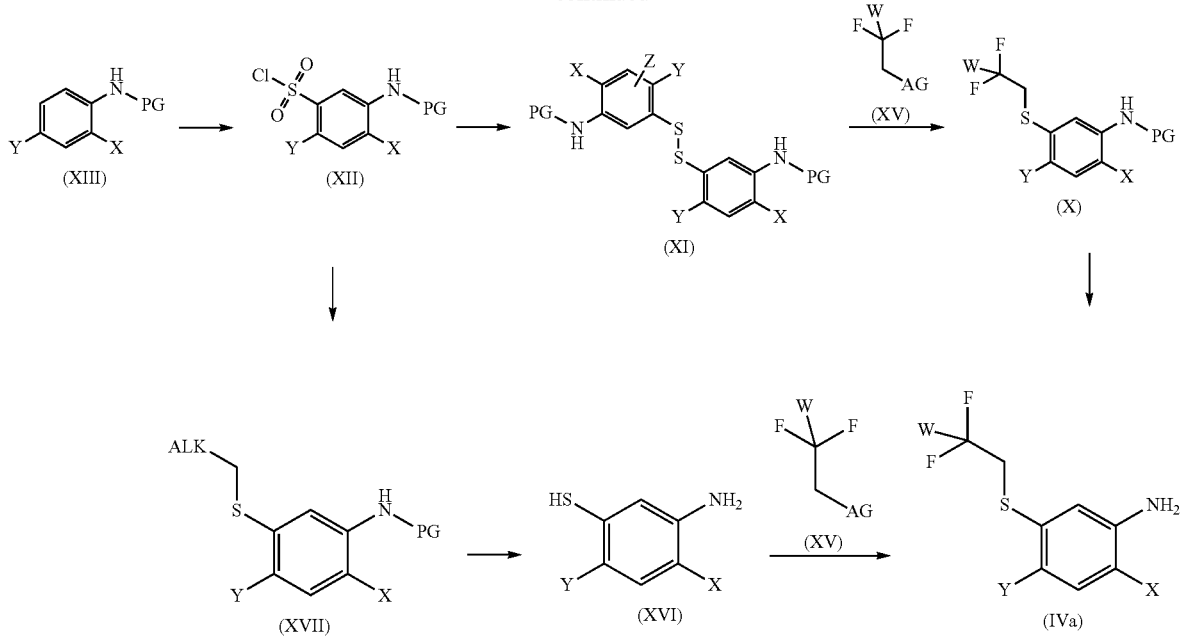

where X, Y and W have the meanings given above, AG represents a leaving group and PG represents a protecting group.

Anilines of the formula (XIV) are either commercially available or can be prepared by known methods. They can be protected with a suitable protective group, for example an acetyl group, to give compounds of the formula (XIII). In the presence of acids, acid anhydrides or acid chlorides, for example, the anilines (XIV) can be converted to the corresponding anilides (XIII). The chlorosulphonation of the protected anilines (XIII) with chlorosulphonic acid gives the corresponding sulphonyl chlorides (XII). The reduction of the sulphonyl chlorides (XII) to the disulphides (XI) is possible by methods known from the literature, for example iron in hydrochloric acid or iodide. The reaction of the disulphides (XI) with haloalkyl electrophiles of the formula (XV) where AG is a leaving group, for example chlorine, bromine, tosylate, mesylate or triflate, gives the sulphides (X). The protecting group can be removed by suitable methods known from the literature, so as to obtain anilines of the formula (IVa).

Instead of the reduction to the disulphide (XI), the sulphonyl chloride (XII) can be reduced with a suitable reducing agent, for example iodine/phosphorus, to give the alkyl thioate (XVII), and then deprotected by a suitable method, for example the reaction with potassium hydroxide solution, to give thiols of the formula (XVI). Reaction of the thiols (XVI) with haloalkyl electrophiles of the formula (XV) where AG represents a leaving group such as, for example, chlorine, bromine, tosylate, mesylate or triflate affords the sulphides (IVa).

Likewise preferably, the thioethers of the formula (IVa) can alternatively be prepared according to the following scheme:

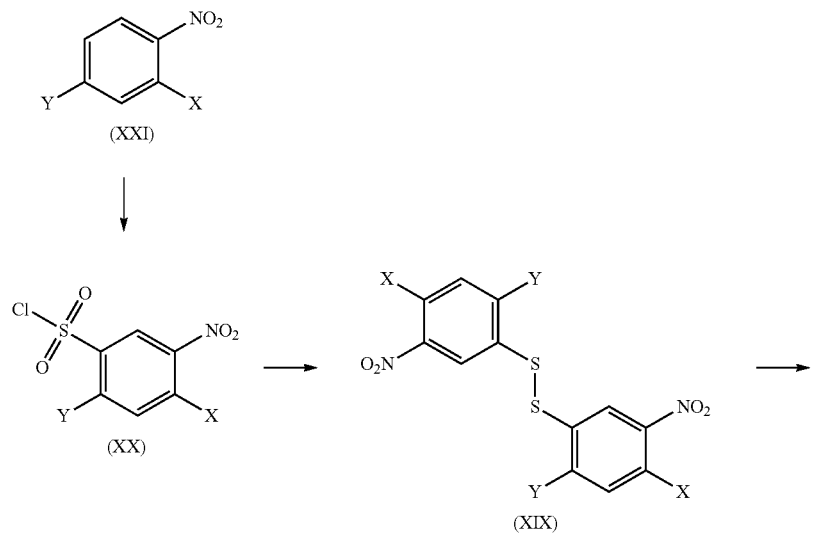

-continued

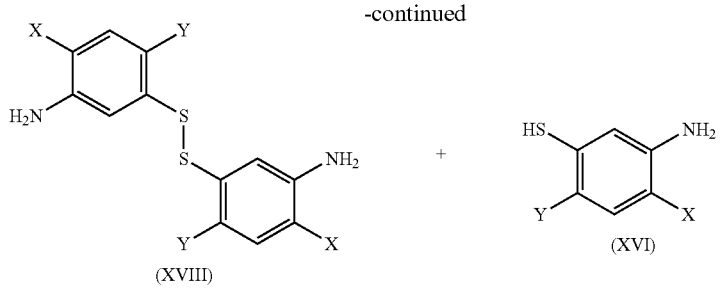

(XVIII)

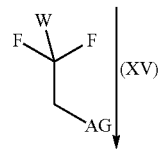

(XVI)

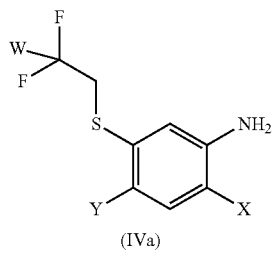

(XV)

(IVa)

where X, Y and W have the meanings given above, AG represents a leaving group and PG represents a protecting group.

The chlorosulphonation of the nitroaromatics of the formula (XXI) with chlorosulphonic acid gives the corresponding sulphonyl chlorides (XX). The reduction of the sulphonyl chlorides (XX) to the bis(nitroaryl) disulphides (XIX) is possible by methods known from the literature, for example iodide. The reduction of the disulphides (XIX) to the disulphanediyldianilines (XVIII), some of which are formed as a mixture with the corresponding aminoarylthiols (XVI), is possible with commonly known reducing agents, for example hydrogen, optionally with the aid of heterogeneous catalysts, for example, Raney nickel, platinum on activated carbon or palladium on activated carbon. Reaction of the disulphides (XVIII) or thiophenols (XVI) with haloalkyl electrophiles of the formula (XV) where AG represents a leaving group such as, for example, chlorine, bromine, iodine, tosylate, mesylate or triflate affords the 3-[(2,2,2-trifluoroethyl)sulphanyl]anilines of the formula (IVa).

Halides of the General Formula (VIIa)

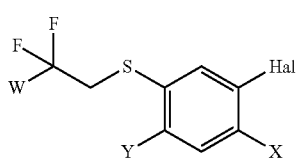

(VIIa)

in which X, Y and W have the meanings given above and Hal represents chlorine, bromine or iodine are known from the literature, from WO 2007/034755, JP 2007/081019, JP 2007/284385, JP 2008/260706, JP 2008/308448, JP 2009/023910 or WO 2012/176856, or can be synthesized by processes known from the literature, which may optionally be slightly modified.

Suitable starting materials for the synthesis of the iodides of the general formula (VIIa) are bromides having the same formula, for example in halogen exchange reactions according to methods known from the literature, if appropriate with metal catalysis (see H. Suzuki, Chem. Let. 1985, 3, 411-412; S. L. Buchwald, J. Amer. Chem. Soc. 2002, 124 (50), 14844-14845). Synthesis is likewise possible proceeding from anilines of the formula (IVa) under Sandmeyer reaction conditions, as described by E. B. Merkushev in Synthesis 1988, 12, 923-937.

Boronic Acids of the General Formula (VIIIa) and (VIIIb)

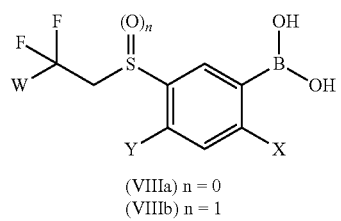

(VIIIa) n = 0
(VIIIb) n = 1 in which X, Y and W have the meanings given above are known from the literature, for example from WO2007/034755, JP2007/284385, JP2009/023910 and WO2012/176856, or can be synthesized by processes known from the literature.

Of particular interest are furthermore intermediates shown in the processes and methods described. These intermediates also form part of the subject matter of the invention. In addition to the intermediates described above, further intermediates are described below.

The Invention Furthermore Provides a Compound of the Formula (IIa)

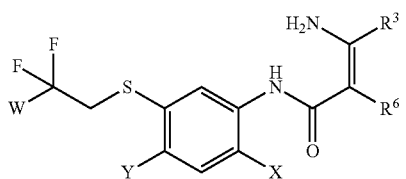

in which $R^3$, $R^6$, W, X and Y have the meanings given above.

Preferred compounds of the formula (IIa) are those in which a combination of the definitions given above as preferred is present, and every embodiment described above as preferred constitutes an independent combination.

More preferred compounds of the formula (IIa) are those in which a combination of the definitions given above as more preferred is present, and every embodiment described above as more preferred constitutes an independent combination.

Particularly preferred compounds of the formula (IIa) are those in which a combination of the definitions given above as particularly preferred is present, and every embodiment described above as particularly preferred constitutes an independent combination.

Very particularly preferred compounds of the formula (IIa) are those in which a combination of the definitions given above as very particularly preferred is present, and every embodiment described above as very particularly preferred constitutes an independent combination.

The compounds of the formula (IIa) can be present in different tautomeric forms. These forms are therefore also embraced, even if not explicitly shown.

The Invention Furthermore Provides a Compound of the Formula (XXXI)

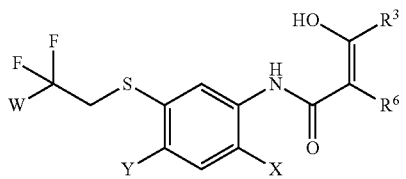

in which $R^3$, $R^6$, W, X and Y have the meanings given above.

Preferred compounds of the formula (XXXI) are those in which a combination of the definitions given above as preferred is present, and every configuration described above as preferred constitutes an independent combination.

More preferred compounds of the formula (XXXI) are those in which a combination of the definitions given above as more preferred is present, and every embodiment described above as more preferred constitutes an independent combination.

Particularly preferred compounds of the formula (XXXI) are those in which a combination of the definitions given above as particularly preferred is present, and every embodiment described above as particularly preferred constitutes an independent combination.

Very particularly preferred compounds of the formula (XXXI) are those in which a combination of the definitions given above as very particularly preferred is present, and every embodiment described above as very particularly preferred constitutes an independent combination.

The compounds of the formula (XXXI) can be present in different tautomeric forms. These forms are therefore also embraced, even if not explicitly shown.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro*, *Aceria kuko*, *Aceria sheldoni*, *Aculops* spp., *Aculus* spp., for example *Aculus fockeui*, *Aculus schlechtendali*, *Amblyomma* spp., *Amphitetranychus viennensis*, *Argas* spp., *Boophilus* spp., *Brevipalpus* spp., for example *Brevipalpus phoenicis*, *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., for example *Eotetranychus hicoriae*, *Epitrimerus pyri*, *Eutetranychus* spp., for example *Eutetranychus banksi*, *Eriophyes* spp., for example *Eriophyes pyri*, *Glycyphagus domesticus*, *Halotydeus destructor*, *Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis*, *Nuphersa* spp., *Oligonychus* spp., for example *Oligonychus coniferarum*, *Oligonychus ilicis*, *Oligonychus indicus*, *Oligonychus mangiferus*, *Oligonychus pratensis*, *Oligonychus punicae*, *Oligonychus yothersi*, *Ornithodorus* spp., *Ornithonyssus* spp., *Panonychus* spp., for example *Panonychus citri* (=*Metatetranychus citri*), *Panonychus ulmi* (=*Metatetranychus ulmi*),

*Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa;* from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis* craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla spp., Aspidiella spp., Aspidiotus spp., for example Aspidiotus nerii, Atanus spp., Aulacorthum solani, Bemisia tabaci, Blastopsylla occidentalis, Boreioglycaspis melaleucae, Brachycaudus helichrysi, Brachycolus spp., Brevicoryne brassicae, Cacopsylla spp., for example Cacopsylla pyricola, Calligypona marginata, Carneocephala fulgida, Ceratovacuna lanigera, Cercopidae, Ceroplastes spp., Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus spp., for example Coccus hesperidum, Coccus longulus, Coccus pseudomagnoliarum, Coccus viridis, Cryptomyzus ribis, Cryptoneossa spp., Ctenarytaina spp., Dalbulus spp., Dialeurodes citri, Diaphorina citri, Diaspis spp., Drosicha spp., Dysaphis spp., for example Dysaphis apiifolia, Dysaphis plantaginea, Dysaphis tulipae, Dysmicoccus spp., Empoasca spp., for example Empoasca abrupta, Empoasca fabae, Empoasca maligna, Empoasca solana, Empoasca stevensi, Eriosoma spp., for example Eriosoma americanum, Eriosoma lanigerum, Eriosoma pyricola, Erythroneura spp., Eucalyptolyma spp., Euphyllura spp., Euscelis bilobatus, Ferrisia spp., Geococcus coffeae, Glycaspis spp., Heteropsylla cubana, Heteropsylla spinulosa, Homalodisca coagulata, Hyalopterus arundinis, Hyalopterus pruni, Icerya spp., for example Icerya purchasi, Idiocerus spp., Idioscopus spp., Laodelphax striatellus, Lecanium spp., for example Lecanium corni (=Parthenolecanium corni), Lepidosaphes spp., for example Lepidosaphes ulmi, Lipaphis erysimi, Lycorma delicatula, Macrosiphum spp., for example Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecanis, Myzus spp., for example Myzus ascalonicus, Myzus cerasi, Myzus ligustri, Myzus ornatus, Myzus persicae, Myzus nicotianae, Nasonovia ribisnigri, Nephotettix spp., for example Nephotettix cincticeps, Nephotettix nigropictus, Nilaparvata lugens, Oncometopia spp., Orthezia praelonga, Oxya chinensis, Pachypsylla spp., Parabemisia myricae, Paratrioza spp., for example Paratrioza cockerelli, Parlatoria spp., Pemphigus spp., for example Pemphigus bursarius, Pemphigus populivenae, Peregrinus maidis, Phenacoccus spp., for example Phenacoccus madeirensis, Phloeomyzus passerinii, Phorodon humuli, Phylloxera spp., for example Phylloxera devastatrix, Phylloxera notabilis, Pinnaspis aspidistrae, Planococcus spp., for example Planococcus citri, Prosopidopsylla flava, Protopulvinaria pyriformis, Pseudaulacaspis pentagona, Pseudococcus spp., for example Pseudococcus calceolariae, Pseudococcus comstocki, Pseudococcus longispinus, Pseudococcus maritimus, Pseudococcus viburni, Psyllopsis spp., Psylla spp., for example Psylla buxi, Psylla mali, Psylla pyri, Pteromalus spp., Pyrilla spp., Quadraspidiotus spp., for example Quadraspidiotus juglansregiae, Quadraspidiotus ostreaeformis, Quadraspidiotus perniciosus, Quesada gigas, Rastrococcus spp., Rhopalosiphum spp., for example Rhopalosiphum maidis, Rhopalosiphum oxyacanthae, Rhopalosiphum padi, Rhopalosiphum rufiabdominale, Saissetia spp., for example Saissetia coffeae, Saissetia miranda, Saissetia neglecta, Saissetia oleae, Scaphoideus titanus, Schizaphis graminum, Selenaspidus articulatus, Sitobion avenae, Sogata spp., Sogatella furcifera, Sogatodes spp., Stictocephala festina, Siphoninus phillyreae, Tenalaphara malayensis, Tetragonocephela spp., Tinocallis caryaefoliae, Tomaspis spp., Toxoptera spp., for example Toxoptera aurantii, Toxoptera citricidus, Trialeurodes vaporariorum, Trioza spp., for example Trioza diospyri, Typhlocyba spp., Unaspis spp., Viteus vitifolii, Zygina spp.;

from the suborder of the Heteroptera, for example Anasa tristis, Antestiopsis spp., Boisea spp., Blissus spp., Calocoris spp., Campylomma livida, Cavelerius spp., Cimex spp., for example Cimex adjunctus, Cimex hemipterus, Cimex lectularius, Cimex pilosellus, Collaria spp., Creontiades dilutus, Dasynus piperis, Dichelops furcatus, Diconocoris hewetti, Dysdercus spp., Euschistus spp., for example Euschistus heros, Euschistus servus, Euschistus tristigmus, Euschistus variolarius, Eurygaster spp., Halyomorpha halys, Heliopeltis spp., Horcias nobilellus, Leptocorisa spp., Leptocorisa varicornis, Leptoglossus occidentalis, Leptoglossus phyllopus, Lygocoris spp., for example Lygocoris pabulinus, Lygus spp., for example Lygus elisus, Lygus hesperus, Lygus lineolaris, Macropes excavatus, Monalonion atratum, Nezara spp., for example Nezara viridula, Oebalus spp., Piesma quadrata, Piezodorus spp., for example Piezodorus guildinii, Psallus spp., Pseudacysta persea, Rhodnius spp., Sahlbergella singularis, Scaptocoris castanea, Scotinophora spp., Stephanitis nashi, Tibraca spp., Triatoma spp.;

from the order of the Hymenoptera, for example Acromyrmex spp., Athalia spp., for example Athalia rosae, Atta spp., Diprion spp., for example Diprion similis, Hoplocampa spp., for example Hoplocampa cookei, Hoplocampa testudinea, Lasius spp., Monomorium pharaonis, Sirex spp., Solenopsis invicta, Tapinoma spp., Urocerus spp., Vespa spp., for example Vespa crabro, Xeris spp.;

from the order of the Isopoda, for example Armadillidium vulgare, Oniscus asellus, Porcellio scaber;

from the order of the Isoptera, for example Coptotermes spp., for example Coptotermes formosanus, Cornitermes cumulans, Cryptotermes spp., Incisitermes spp., Microtermes obesi, Odontotermes spp., Reticulitermes spp., for example Reticulitermes flavipes, Reticulitermes hesperus;

from the order of the Lepidoptera, for example Achroia grisella, Acronicta major, Adoxophyes spp., for example Adoxophyes orana, Aedia leucomelas, Agrotis spp., for example Agrotis segetum, Agrotis ipsilon, Alabama spp., for example Alabama argillacea, Amyelois transitella, Anarsia spp., Anticarsia spp., for example Anticarsia gemmatalis, Argyroploce spp., Barathra brassicae, Borbo cinnara, Bucculatrix thurberiella, Bupalus piniarius, Busseola spp., Cacoecia spp., Caloptilia theivora, Capua reticulana, Carpocapsa pomonella, Carposina niponensis, Cheimatobia brumata, Chilo spp., for example Chilo plejadellus, Chilo suppressalis, Choristoneura spp., Clysia ambiguella, Cnaphalocerus spp., Cnaphalocrocis medinalis, Cnephasia spp., Conopomorpha spp., Conotrachelus spp., Copitarsia spp., Cydia spp., for example Cydia nigricana, Cydia pomonella, Dalaca noctuides, Diaphania spp., Diatraea saccharalis, Earias spp., Ecdytolopha aurantium, Elasmopalpus lignosellus, Eldana saccharina, Ephestia spp., for example Ephestia elutella, Ephestia kuehniella, Epinotia spp., Epiphyas postvittana, Etiella spp., Eulia spp., Eupoecilia ambiguella, Euproctis spp., for example Euproctis chrysorrhoea, Euxoa spp., Feltia spp., Galleria mellonella, Gracillaria spp., Grapholitha spp., for example Grapholita molesta, Grapholita prunivora, Hedylepta spp., Helicoverpa spp., for example Helicoverpa armigera, Helicoverpa zea, Heliothis spp., for example Heliothis virescens, Hofmannophila pseudospretella, Homoeosoma spp., Homona spp., Hyponomeuta padella, Kakivoria flavofasciata, Laphygma spp., Leucinodes orbonalis, Leucoptera spp., for example

*Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., *for example Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Anion* spp., for example *Anion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, *Angiostrongylus* spp., *Anisakis* spp., *Anoplocephala* spp., *Ascaris* spp., *Ascaridia* spp., *Baylisascaris* spp., *Brugia* spp., *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., *Diphyllobothrium* spp., *Dipylidium* spp., *Dirofilaria* spp., *Dracunculus* spp., *Echinococcus* spp., *Echinostoma* spp., *Enterobius* spp., *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., *Hyostrongylus* spp., *Litomosoides* spp., *Loa* spp., *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., *Strongylus* spp., *Syngamus* spp., *Taenia* spp., *Teladorsagia* spp., *Thelazia* spp., *Toxascaris* spp., *Toxocara* spp., *Trichinella* spp., *Trichobilharzia* spp., *Trichostrongylus* spp., *Trichuris* spp., *Uncinaria* spp., *Wuchereria* spp.;

plant pests from the phylum of the Nematoda, i.e. phytoparasitic nematodes, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., *for example Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., *for example Trichodorus obtusus, Trichodorus primitivius, Tylenchorhynchus* spp., *for example Tylenchorhynchus annulatus, Tylenchulus* spp., for example *Tylenchulus semipenetrans, Xiphinema* spp., for example *Xiphinema index.*

In addition, it is possible to control, from the sub-kingdom of the Protozoa, the order of the Coccidia, for example *Eimeria* spp.

Nematodes

In the present context, the term "nematodes" comprises all species of the phylum Nematoda and here in particular species acting as parasites on plants or fungi (for example species of the order Aphelenchida, *Meloidogyne*, Tylenchida and others) or else on humans and animals (for example species of the orders Trichinellida, Tylenchida, Rhabditida and Spirurida) and causing damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per soil volume, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, particularly preferably 51-79% and very particularly preferably the complete kill or the complete prevention of development and growth of the nematodes by a reduction of 80 to 100%. The control of nematodes as described herein also comprises the control of proliferation of the nematodes (development of cysts and/or eggs). Compounds of the formula (I) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp., *Criconemoides ferniae*, *Criconemoides onoense*, *Criconemoides ornatum* and *Criconemoides* spp., *Ditylenchus destructor*, *Ditylenchus dipsaci*, *Ditylenchus myceliophagus* and also the stem and leaf endoparasites *Ditylenchus* spp., *Dolichodorus heterocephalus*, *Globodera pallida* (=*Heterodera pallida*), *Globodera rostochiensis* (yellow potato cyst nematode), *Globodera solanacearum*, *Globodera tabacum*, *Globodera virginia* and the non-migratory cyst-forming parasites *Globodera* spp., *Helicotylenchus digonicus*, *Helicotylenchus dihystera*, *Helicotylenchus erythrine*, *Helicotylenchus multicinctus*, *Helicotylenchus nannus*, *Helicotylenchus pseudorobustus* and *Helicotylenchus* spp., *Hemicriconemoides*, *Hemicycliophora arenaria*, *Hemicycliophora nudata*, *Hemicycliophora parvana*, *Heterodera avenae*, *Heterodera cruciferae*, *Heterodera glycines* (soya bean cyst nematode), *Heterodera oryzae*, *Heterodera schachtii*, *Heterodera zeae* and the non-migratory cyst-forming parasites *Heterodera* spp., *Hirschmaniella gracilis*, *Hirschmaniella oryzae*, *Hirschmaniella spinicaudata* and the stem and leaf endoparasites *Hirschmaniella* spp., *Hoplolaimus aegyptii*, *Hoplolaimus californicus*, *Hoplolaimus columbus*, *Hoplolaimus galeatus*, *Hoplolaimus indicus*, *Hoplolaimus magnistylus*, *Hoplolaimus pararobustus*, *Longidorus africanus*, *Longidorus breviannulatus*, *Longidorus elongatus*, *Longidorus laevicapitatus*, *Longidorus vineacola* and the ectoparasites *Longidorus* spp., *Meloidogyne acronea*, *Meloidogyne africana*, *Meloidogyne arenaria*, *Meloidogyne arenaria thamesi*, *Meloidogyne artiella*, *Meloidogyne chitwoodi*, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuyensis*, *Meloidogyne minor*, *Meloidogyne naasi*, *Meloidogyne paranaensis*, *Meloidogyne thamesi* and the non-migratory parasites *Meloidogyne* spp., *Meloinema* spp., *Nacobbus aberrans*, *Neotylenchus vigissi*, *Paraphelenchus pseudoparietinus*, *Paratrichodorus allius*, *Paratrichodorus lobatus*, *Paratrichodorus minor*, *Paratrichodorus nanus*, *Paratrichodorus porosus*, *Paratrichodorus teres* and *Paratrichodorus* spp., *Paratylenchus hamatus*, *Paratylenchus minutus*, *Paratylenchus projectus* and *Paratylenchus* spp., *Pratylenchus agilis*, *Pratylenchus alleni*, *Pratylenchus andinus*, *Pratylenchus brachyurus*, *Pratylenchus cerealis*, *Pratylenchus coffeae*, *Pratylenchus crenatus*, *Pratylenchus delattrei*, *Pratylenchus giibbicaudatus*, *Pratylenchus goodeyi*, *Pratylenchus hamatus*, *Pratylenchus hexincisus*, *Pratylenchus loosi*, *Pratylenchus neglectus*, *Pratylenchus penetrans*, *Pratylenchus pratensis*, *Pratylenchus scribneri*, *Pratylenchus teres*, *Pratylenchus thomei*, *Pratylenchus vulnus*, *Pratylenchus zeae* and the migratory endoparasites *Pratylenchus* spp., *Pseudohalenchus minutus*, *Psilenchus magnidens*, *Psilenchus tumidus*, *Punctodera chalcoensis*, *Quinisulcius acutus*, *Radopholus citrophilus*, *Radopholus similis*, the migratory endoparasites *Radopholus* spp., *Rotylenchulus borealis*, *Rotylenchulus parvus*, *Rotylenchulus reniformis* and *Rotylenchulus* spp., *Rotylenchus laurentinus*, *Rotylenchus macrodoratus*, *Rotylenchus robustus*, *Rotylenchus uniformis* and *Rotylenchus* spp., *Scutellonema brachyurum*, *Scutellonema bradys*, *Scutellonema clathri-*

*caudatum* and the migratory endoparasites *Scutellonema* spp., *Subanguina radiciola*, *Tetylenchus nicotianae*, *Trichodorus cylindricus*, *Trichodorus minor*, *Trichodorus primitivus*, *Trichodorus proximus*, *Trichodorus similis*, *Trichodorus sparsus* and the ectoparasites *Trichodorus* spp., *Tylenchorhynchus agri*, *Tylenchorhynchus brassicae*, *Tylenchorhynchus clarus*, *Tylenchorhynchus claytoni*, *Tylenchorhynchus digitatus*, *Tylenchorhynchus* ebriensis, *Tylenchorhynchus* maximus, *Tylenchorhynchus* nudus, *Tylenchorhynchus* vulgaris and *Tylenchorhynchus* spp., *Tylenchulus semipenetrans* and the semiparasites *Tylenchulus* spp., *Xiphinema americanum*, *Xiphinema brevicolle*, *Xiphinema dimorphicaudatum*, *Xiphinema index* and the ectoparasites *Xiphinema* spp.

Nematodes for the control of which a compound of the formula (I) may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*) and beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) can be used include plants such as cereals (for example rice, barley, wheat, rye, oats, maize and the like), beans (soya bean, aduki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plant for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular *Pratylenchus brachyurus*, *Pratylenchus coffeae*, *Meloidogyne exigua*, *Meloidogyne incognita*, *Meloidogyne coffeicola*, *Helicotylenchus* spp. and also *Meloidogyne paranaensis*, *Rotylenchus* spp., *Xiphinema* spp., *Tylenchorhynchus* spp. and *Scutellonema* spp.

The compounds of the formula (I) are particularly suitable for controlling potato nematodes, in particular *Pratylenchus brachyurus*, *Pratylenchus pratensis*, *Pratylenchus scribneri*, *Pratylenchus penetrans*, *Pratylenchus coffeae*, *Ditylenchus dipsaci* and of *Pratylenchus alleni*, *Pratylenchus andinus*, *Pratylenchus cerealis*, *Pratylenchus crenatus*, *Pratylenchus hexincisus*, *Pratylenchus loosi*, *Pratylenchus neglectus*, *Pratylenchus teres*, *Pratylenchus thornei*, *Pratylenchus vulnus*, *Belonolaimus longicaudatus*, *Trichodorus cylindricus*, *Trichodorus primitivus*, *Trichodorus proximus*, *Trichodorus similis*, *Trichodorus sparsus*, *Paratrichodorus minor*, *Paratrichodorus allius*, *Paratrichodorus nanus*, *Paratrichodorus teres*, *Meloidogyne arenaria*, *Meloidogyne fallax*, *Meloidogyne hapla*, *Meloidogyne thamesi*, *Meloidogyne incognita*, *Meloidogyne chitwoodi*, *Meloidogyne javanica*, *Nacobbus aberrans*, *Globodera rostochiensis*, *Globodera pallida*, *Ditylenchus destructor*, *Radopholus similis*, *Rotylenchulus reniformis*, *Neotylenchus vigissi*, *Paraphelenchus pseudoparietinus*, *Aphelenchoides fragariae* and *Meloinema* spp.

The compounds of the formula (I) are particularly suitable for controlling tomato nematodes, in particular *Meloidogyne arenaria*, *Meloidogyne hapla*, *Meloidogyne javanica*, *Meloidogyne incognita*, *Pratylenchus penetrans* and also *Pratylenchus brachyurus*, *Pratylenchus coffeae*, *Pratylenchus scribneri*, *Pratylenchus vulnus*, *Paratrichodorus minor*, *Meloidogyne exigua*, *Nacobbus aberrans*, *Globodera solanacearum*, *Dolichodorus heterocephalus* and *Rotylenchulus reniformis*.

The compounds of the formula (I) are particularly suitable for controlling cucumber plant nematodes, in particular *Meloidogyne arenaria*, *Meloidogyne hapla*, *Meloidogyne javanica*, *Meloidogyne incognita*, *Rotylenchulus reniformis* and *Pratylenchus thornei*.

The compounds of the formula (I) are particularly suitable for controlling cotton nematodes, in particular *Belonolaimus longicaudatus*, *Meloidogyne incognita*, *Hoplolaimus columbus*, *Hoplolaimus galeatus* and *Rotylenchulus reniformis*.

The compounds of the formula (I) are particularly suitable for controlling maize nematodes, in particular *Belonolaimus longicaudatus*, *Paratrichodorus minor* and also *Pratylenchus brachyurus*, *Pratylenchus delattrei*, *Pratylenchus hexincisus*, *Pratylenchus penetrans*, *Pratylenchus zeae*, (*Belonolaimus gracilis*), *Belonolaimus nortoni*, *Longidorus breviannulatus*, *Meloidogyne arenaria*, *Meloidogyne arenaria thamesi*, *Meloidogyne graminis*, *Meloidogyne incognita*, *Meloidogyne incognita acrita*, *Meloidogyne javanica*, *Meloidogyne naasi*, *Heterodera avenae*, *Heterodera oryzae*, *Heterodera zeae*, *Punctodera chalcoensis*, *Ditylenchus dipsaci*, *Hoplolaimus aegyptii*, *Hoplolaimus magnistylus*, *Hoplolaimus galeatus*, *Hoplolaimus indicus*, *Helicotylenchus digonicus*, *Helicotylenchus dihystera*, *Helicotylenchus pseudorobustus*, *Xiphinema americanum*, *Dolichodorus heterocephalus*, *Criconemella ornata*, *Criconemella onoensis*, *Radopholus similis*, *Rotylenchulus borealis*, *Rotylenchulus parvus*, *Tylenchorhynchus agri*, *Tylenchorhynchus clarus*, *Tylenchorhynchus claytoni*, *Tylenchorhynchus maximus*, *Tylenchorhynchus nudus*, *Tylenchorhynchus vulgaris*, *Quinisulcius acutus*, *Paratylenchus minutus*, *Hemicycliophora*

*parvana, Aglenchus agricola, Anguina tritici, Aphelenchoides arachidis, Scutellonema brachyurum* and *Subanguina radiciola*.

The compounds of the formula (I) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans*.

The compounds of the formula (I) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum*.

The compounds of the formula (I) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans*.

The compounds of the formula (I) are particularly suitable for controlling nematodes in tree crops—pome fruit, in particular *Pratylenchus penetrans* and also *Pratylenchus vulnus, Longidorus elongatus, Meloidogyne incognita* and *Meloidogyne hapla*.

The compounds of the formula (I) are particularly suitable for controlling nematodes in tree crops—stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus*.

The compounds of the formula (I) are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp, *Xiphinema* spp. and *Cacopaurus pestis*.

In the present context, the term "nematodes" also refers to nematodes damaging humans or animals.

Specific nematode species harmful to humans or to animals are:

*Trichinellida*, for example: *Trichuris* spp., *Capillaria* spp., *Paracapillaria* spp., *Eucoleus* spp., *Trichomosoides* spp., *Trichinella* spp.;

From the order of the Tylenchida, for example: *Micronema* spp., *Strongyloides* spp.

From the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelminthes (e.g. Monogenea, cestodes and trematodes), Acanthocephala and Pentastoma. The following helminths may be mentioned as being preferred:

Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.

From the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diochis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the *Moniliformida*, for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal husbandry, the administration of the compounds of the formula (I) is carried out by methods generally known in the art, directly or enterally, parenterally, dermally or nasally in the form of suitable preparations. Administration may be prophylactic or therapeutic.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (rickettsia-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkyl sulphonates, alkylsulphates, arylsulphonates, protein hydrolyzates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I), with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides:

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulphan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulphoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulphotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulphan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulphoxaflor.

(5) Allosteric activators of the nicotinergic acetylcholine receptor (nAChR), for example spinosyns, e.g. spinetoram and spinosad.

(6) Chloride channel activators, for example, avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active compounds with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulphluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon; or acequinocyl; or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active compounds, for example afidopyropen, azadirachtin, benclothiaz, benzoximate, bifenazate, bromopropylate, chinomethionat, cryolite, dicofol, diflovidazin, fluensulphone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on Bacillus firmus (1-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro [indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5 S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example; http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxypheny)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl) [1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin (7) Amino acid and protein biosynthesis inhibitors, for example (7.1) andoprim, (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors, for example (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) meptyldinocap.

(15) Further compounds such as, for example, (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulphamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulphamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulphocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2, 4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino- 5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N41-(2,4,6-trichlorophenyl)propan-2-yl-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluoropheny)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazole-5-amine. All the mixing partners mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain 1-1582 (Accession number CNCM 1-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Acession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accesion No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM 1-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suilins* spp., *Streptomyces* spp.

Examples of plant extracts and products formed by microorganisms, including proteins and secondary metabolites, which are used or can be used as biological pesticides are: *Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, *Quillaja*, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safeners as Mixing Components

The compounds of the formula (I) can be combined with safeners such as, for example, benoxacor, cloquintocet (-mexyl), cyometrinil, cyprosulphamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and parts of plants can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvement. However, the treatment of seed entails a series of problems which cannot always be solved in a satisfactory manner Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of crop protection products.

The present invention therefore in particular also relates to a method for the protection of seed and germinating plants, from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions or compounds of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis.*

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical compounds. Preference is given to using alkyl naphthalenesulphonates, such as diisopropyl or diisobutyl naphthalenesulphonates.

Suitable dispersants and/or emulsifiers which may be present in the seed dressing formulations usable in accordance with the invention are all nonionic, anionic and cationic dispersants conventionally used for the formulation of active agrochemical compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical compounds. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Preferred examples include cellulose derivatives, acrylic acid derivatives, xanthan, modified clays and finely divided silica.

Useful adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, cage birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi-host ticks); from the order of *Mesostigmata* like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombicula* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa include:

Mastigophora (*Flagellata*), for example Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example, *Giardia lamblia, G. canis*;

Sarcomastigophora (Rhizopoda) such as Entamoebidae, for example, *Entamoeba histolytica*, Hartmanellidae, for example, *Acanthamoeba* sp., *Harmanella* sp.;

Apicomplexa (Sporozoa) such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii*, *Globidium* spec., *Isospora belli, I. canis, I. felis, I. ohioensis, I. rivolta, I. spec., I. suis, Cystisospora* spec., *Cryptosporidium* spec., in particular *C. parvum*; such as Toxoplasmadiae, for example, *Toxoplasma gondii, Hammondia heydornii, Neospora caninum, Besnoitia besnoitii*; such as Sarcocystidae, for example, *Sarcocystis bovicanis, S. bovihominis, S. ovicanis, S. ovifelis, S. neurona, S. spec., S. suihominis*, such as Leucozoidae, for example, *Leucozytozoon simondi*, such as Plasmodiidae, for example, *Plasmodium berghei, P. falciparum, P. malariae, P. ovale, P. vivax, P. spec.*, such as Piroplasmea, for example, *Babesia argentina, B. bovis, B. canis, B. spec., Theileria parva, Theileria* spec., such as Adeleina, for example, *Hepatozoon canis, H. spec.*

Pathogenic endoparasites, which are helminths, include Platyhelmintha (e.g. Monogenea, cestodes and trematodes), roundworms, Acanthocephala, and Pentastoma. These include:

monogenea: for example: *Gyrodactylus* spp., *Dactylogyrus* spp., *Polystoma* spp.;

cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diochis* spp., *Dipylidium* spp., *Joyeuxiella* spp., *Diplopylidium* spp.;

trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

roundworms: Trichinellida, for example: *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the *Moniliformida*, for example *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal husbandry, in animal breeding, in buildings for live stock and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in buildings for live stock or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclophenol, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

Anopheles: malaria, filariasis;

Culex: Japanese encephalitis, filariasis, other viral diseases, transmission of worms;

Aedes: yellow fever, dengue fever, filariasis, other viral diseases;

Simuliidae: transmission of worms, in particular Onchocerca volvulus;

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as *Borrelia duttoni*, tick-borne encephalitis, Q fever (*Coxiella burnetii*), babesioses (*Babesia canis canis*).

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

EXAMPLES

Elucidation of the Processes and Intermediates

The preparation and use examples which follow illustrate the invention without limiting it. The products were characterized by means of 1H NMR spectroscopy and/or LC-MS (liquid chromatography-mass spectrometry) and/or GC-MS (gas chromatography-mass spectrometry).

The log P values were determined analogously to OECD Guideline 117 (EC Directive 92/69/EEC) by HPLC (high-performance liquid chromatography) using reversed-phase columns (C 18), by the following methods:
[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile. log P[b] is also referred to as log P(HCOOH).
[b] LC-MS determination in the neutral range is effected at pH 7.8 with 0.001 molar aqueous ammonium hydrogencarbonate solution and acetonitrile as eluents; linear gradient from 10% acetonitrile to 95% acetonitrile. log P[1] is also referred to as log P(neutral).

Calibration is effected with solutions of a homologous series of unbranched alkan-2-ones (having 3 to 16 carbon atoms) with known log P values (log P values determined on the basis of the retention times by linear interpolation between two successive alkanones).

The NMR spectra were measured with a Bruker II Avance 400 equipped with a 1.7 mm TCI probe head. In isolated cases, the NMR spectra were determined using a Bruker Avance II 600.

The NMR data for selected examples are listed in conventional form (δ values, multiplet splitting, number of hydrogen atoms). The splitting of the signals was described as follows: s (singlet), d (doublet), t (triplet), q (quartet), m (multiplet), broad (for broad signals). Solvents used were CD$_3$CN, CDCl$_3$ or D6-DMSO, and tetramethylsilane (0.00 ppm) was used as reference.

The GC-MS spectra are determined using an Agilent 6890 GC, HP 5973 MSD on a dimethylsilicone phase, using a temperature gradient from 50° C. to 320° C. GC-MS indices are determined as Kovats indices using solutions of a homologous series of n-alkanes (having an even number of 8 to 38 carbon atoms).

Preparation Example 1: 3-{2-Fluoro-4-methyl-5-[(2,2,2-trifluoroethyl)sulphinyl]phenyl}-6-(trifluoromethyl)pyrimidin-4(3H)-one (Ex. No. 2)

Step 1: 4,4,4-Trifluoro-N-{2-fluoro-4-methyl-5-[(2,2,2-trifluoroethyl)sulphanyl]phenyl}-3-hydroxybut-2-enamide (Ex. No. XXXI-1)

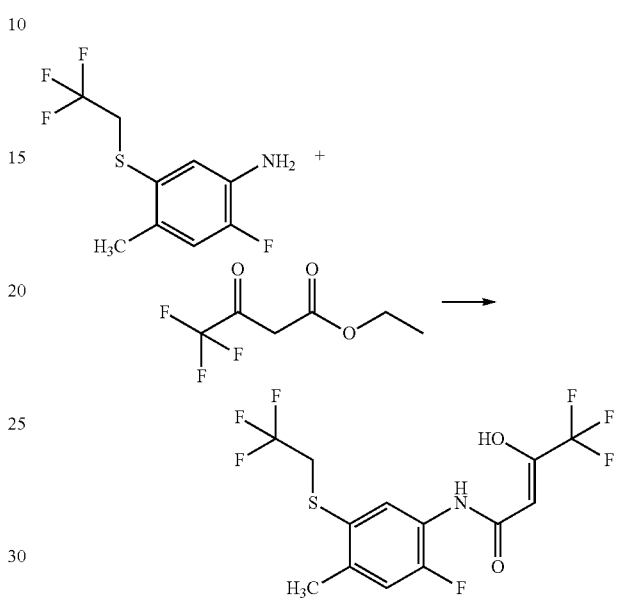

2 g (8.36 mmol) of 2-fluoro-4-methyl-5-[(2,2,2-trifluoroethyl)sulphanyl]aniline were initially charged in 42 ml of toluene. 2.48 ml (16.7 mmol) of ethyl 4,4,4-trifluoroacetoacetate and 20.4 mg (0.16 mmol) of 4-DMAP were added and the reaction mixture was heated under reflux for 14 h. After cooling of the reaction mixture, the solvent was removed under reduced pressure on a rotary evaporator and the residue (3.45 g) was converted into Step 2 without further purification.
log P(HCOOH): 2.77

Step 2: 3-Amino-4,4,4-trifluoro-N-{2-fluoro-4-methyl-5-[(2,2,2-trifluoroethyl)sulphanyl]phenyl}but-2-enamide (Ex. No. IIa-1)

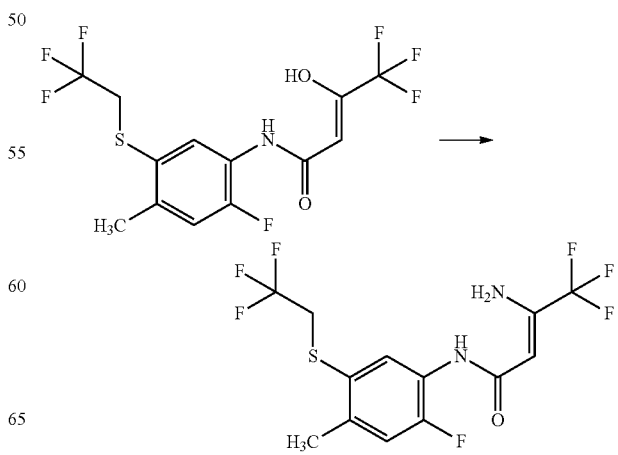

The residue (3.45 g) was taken up in ethyl acetate (37.5 ml), and ammonium acetate (4.51 g, 58.5 mmol) was added. The reaction mixture was heated under reflux for 7 h. After cooling of the reaction mixture, ethyl acetate (64 ml) was added and the organic phase was washed first with water and then with saturated NaCl solution. The organic phase was dried with MgSO₄ and the solvent was removed under reduced pressure on a rotary evaporator. The residue (2.78 g) was converted without further purification into Step 3.

log P(HCOOH): 3.61

Step 3: 3-{2-Fluoro-4-methyl-5-[(2,2,2-trifluoroethyl)sulphanyl]phenyl}-6-(trifluoromethyl)pyrimidin-4(3H)-one (Ex. No. 1)

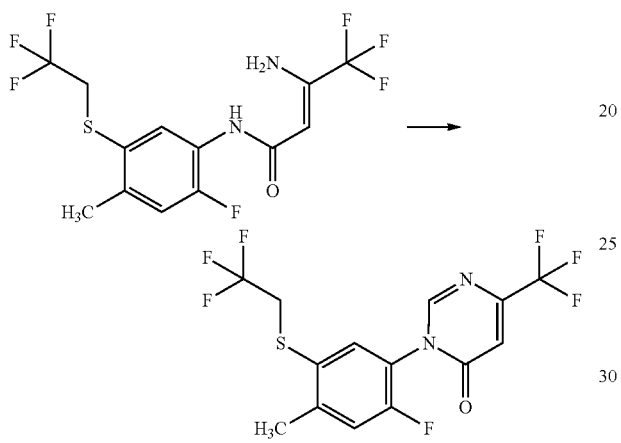

The residue (2.78 g) was taken up in DMF-DMA (6.2 g) and stirred at 100° C. for 7 h. After cooling of the reaction mixture, the solvent was removed under reduced pressure on a rotary evaporator and the residue was taken up in formic acid (17 ml). The reaction mixture was heated under reflux for 2 h. After cooling of the reaction mixture, the solvent was removed under reduced pressure on a rotary evaporator and ethyl acetate was added to the residue. The organic phase was washed with water and dried with MgSO₄. The solvent was removed under reduced pressure on a rotary evaporator and the residue was purified by MPLC (cyclohexane/acetone). This gave 670 mg of the title compound (27% of theory over the 3 steps, purity 80% according to LC-MS). Further purification by MPLC (cyclohexane/ethyl acetate) gave 157 mg of the title compound of a better purity (100% according to LC-MS).

¹H-NMR (D6-DMSO) δ ppm: 8.72 (s, 1H), 7.89 (d, 1H), 7.48 (d, 1H), 7.17 (s, 1H), 4.01 (q, 2H), 2.44 (s, 3H)

log P(HCOOH): 3.42 log P(neutral): 3.4

Step 4: 3-{2-Fluoro-4-methyl-5-[(2,2,2-trifluoroethyl)sulphinyl]phenyl}-6-(trifluoromethyl)pyrimidin-4(3H)-one (Ex. No. 2)

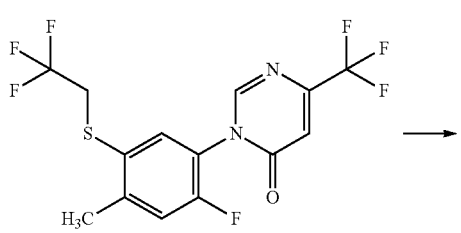

-continued

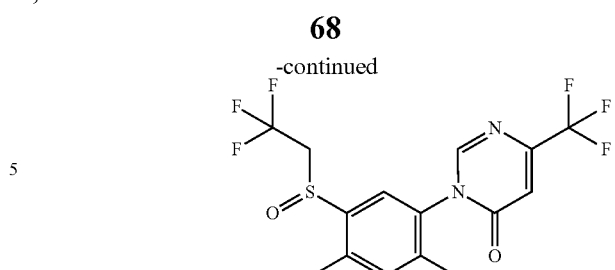

190 mg (0.492 mmol) of 3-{2-fluoro-4-methyl-5-[(2,2,2-trifluoroethyl)sulphanyl]phenyl}-6-(trifluoromethyl)pyrimidin-4(3H)-one were initially charged in methylene chloride, 124 mg (0.541 mmol) of meta-chloroperbenzoic acid were added and the reaction mixture was stirred at 0° C. for 3 h and then extracted with sodium thiosulphate and sodium bicarbonate solution. The organic phase was dried over magnesium sulphate and filtered. Removal of the solvent under reduced pressure gave 170 mg of the title compound (84% of theory, purity 97% according to LC/MS).

¹H-NMR (D6-DMSO) δ ppm: 8.75 (s, 1H), 8.17 (d, 1H), 7.59 (d, 1H), 7.17 (s, 1H), 4.29-4.22 (m, 1H), 4.07-4.01 (m, 1H), 2.48 (s, 3H)

log P(HCOOH): 2.4 log P(neutral): 2.38

Preparation Example 2: 3-[2,4-Dimethyl-5-(2,2,2-trifluoroethylsulphinyl)phenyl]-6-(trifluoromethyl)pyrimidin-4-one (Ex. No. 6)

Step 1: N-[2,4-Dimethyl-5-(2,2,2-trifluoroethylsulphanyl)phenyl]-4,4,4-trifluoro-3-hydroxybut-2-enamide (Ex. No. XXXI-2)

5 g (21.2 mmol) of 2,4-dimethyl-5-[(2,2,2-trifluoroethyl)sulphanyl]aniline were initially charged in 42 ml of toluene. 6.21 ml (42.5 mmol) of ethyl 4,4,4-trifluoroacetoacetate and 51.9 mg (0.42 mmol) of 4-DMAP were added and the reaction mixture was heated under reflux for 14 h. After cooling of the reaction mixture, the solvent was removed under reduced pressure on a rotary evaporator and the residue (7.93 g) was converted into Step 2 without further purification.

log P(HCOOH): 2.87

Step 2: 3-Amino-N-[2,4-dimethyl-5-(2,2,2-trifluoro-ethylsulphanyl)phenyl]-4,4,4-trifluorobut-2-enamide
(Ex.-No. IIa-2)

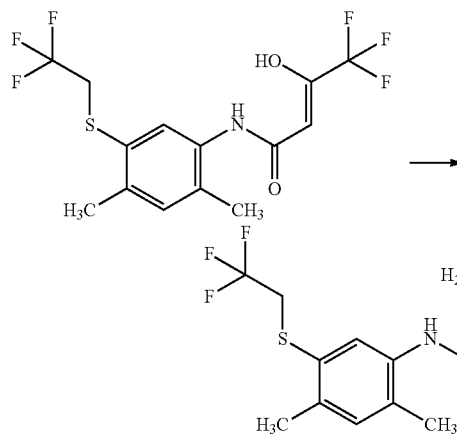

The residue (7.93 g) was taken up in ethyl acetate (82.8 ml), and ammonium acetate (6.68 g, 86.6 mmol) was added. The reaction mixture was heated under reflux for 7 h. After cooling of the reaction mixture, the solvent was removed under reduced pressure on a rotary evaporator. The residue (7.91 g) was converted without further purification into Step 3.

log P(HCOOH): 3.63

Step 3: 3-[2,4-Dimethyl-5-(2,2,2-trifluoroethylsulphanyl)phenyl]-6-(trifluoromethyl)pyrimidin-4-one
(Ex. No. 5)

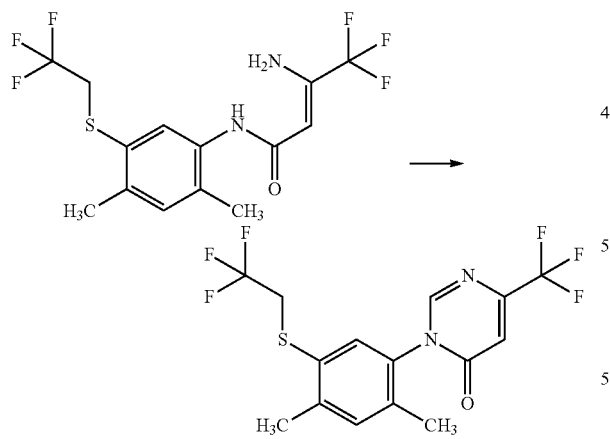

The residue (7.91 g) was taken up in triethyl orthoformate (53 ml), and sulphuric acid (0.33 ml) was added. The mixture was stirred at 140° C. for 3 h. After cooling of the reaction mixture, the solvent was removed under reduced pressure on a rotary evaporator. Water was added to the residue and the mixture was extracted with ethyl acetate. The organic phase was dried over $Na_2SO_4$ and filtered. The solvent was removed under reduced pressure on a rotary evaporator and the residue was purified by MPLC (cyclohexane/acetone). This gave 2.99 g of the title compound (37% of theory over the 3 steps, purity 96% according to LC-MS).

$^1$H-NMR (D6-DMSO) δ ppm: 8.59 (s, 1H), 7.64 (s, 1H), 7.33 (s, 1H), 7.13 (s, 1H), 4.00 (q, 2H), 2.38 (s, 3H), 2.04 (s, 3H)

log P(HCOOH): 3.56 log P(neutral): 3.5

Step 4: 3-[2,4-Dimethyl-5-(2,2,2-trifluoroethylsulphinyl)phenyl]-6-(trifluoromethyl)pyrimidin-4-one
(Ex. No. 6)

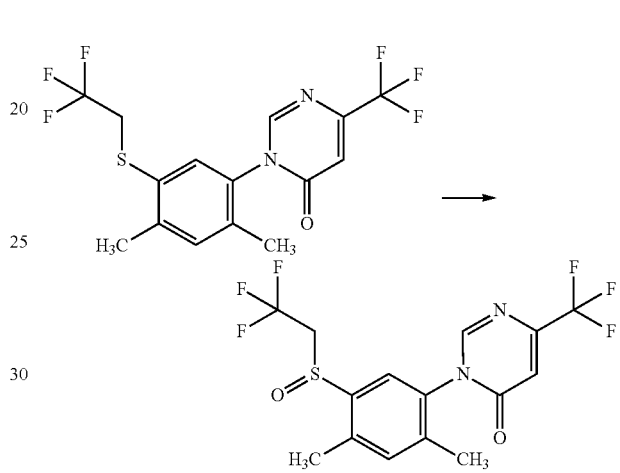

500 mg (1.30 mmol) of 3-[2,4-Dimethyl-5-(2,2,2-trifluoroethylsulphanyl)phenyl]-6-(trifluoromethyl)-pyrimidin-4-one were initially charged in methylene chloride (25 ml), 331 mg (1.43 mmol) of meta-chloroperbenzoic acid were added and the reaction mixture was stirred at 0° C. for 1 h and then washed with sodium thiosulphate and sodium bicarbonate solution. The organic phase was dried over sodium sulphate and filtered. Removal of the solvent under reduced pressure gave 490 mg of the title compound (92% of theory, purity 98% according to LC/MS).

$^1$H-NMR (D6-DMSO) δ ppm: 8.64-8.62 (m, 1H), 7.92 (s, 1H), 7.47-7.44 (m, 1H), 7.13 (s, 1H), 4.30-3.88 (m, 2H), 2.43 (s, 3H), 2.15 (s, 3H)

log P(HCOOH): 2.43 log P(neutral): 2.39

The enantiomers were obtained from the racemate by separating them preparatively by HPLC on a chiral column (ChiralCel OJ-H, e.g. 5 nm 250×4.6 mm) using the mobile phase heptane/methanol/ethanol.

The optical rotations were determined on a Perkin Elmer 341, serial number 9123, at a wavelength of 589 nm and a temperature of 20° C.

The specific optical rotations below should be understood as an average from 5 different measurements:

Enantiomer 1 (Ex. No. 56): 89.5 in $CHCl_3$ (c=0.022)
Enantiomer 2 (Ex. No. 49): −87.8 in $CHCl_3$ (c=0.019)

By the above-described processes, the following compounds of the formula (I) were prepared.

TABLE 1

Compounds of the formula (I) having the substructure (I-A)

W = F and V = O

| Compound number | n | Y | X | R$^5$ | R$^3$ | R$^6$ |
|---|---|---|---|---|---|---|
| 1 | 0 | CH$_3$ | F | H | CF$_3$ | H |
| 2 | 1 | CH$_3$ | F | H | CF$_3$ | H |
| 3 | 0 | Cl | Cl | H | CF$_3$ | H |
| 4 | 1 | Cl | Cl | H | CF$_3$ | H |
| 5 | 0 | CH$_3$ | CH$_3$ | H | CF$_3$ | H |
| 6 | 1 | CH$_3$ | CH$_3$ | H | CF$_3$ | H |
| 7 | 1 | CH$_3$ | F | H | c-Pr | H |
| 8 | 0 | CH$_3$ | F | CH$_3$ | CF$_3$ | H |
| 9 | 0 | CH$_3$ | F | H | CF$_2$CF$_3$ | H |
| 10 | 1 | CH$_3$ | F | H | CH$_2$CH$_3$ | H |
| 11 | 1 | CH$_3$ | F | H | Phenyl | H |
| 12 | 0 | CH$_3$ | H | H | H | F |
| 13 | 0 | CH$_3$ | CH$_3$ | H | CH$_3$ | CH$_3$ |
| 14 | 1 | CH$_3$ | CH$_3$ | CH$_3$ | CF$_3$ | H |
| 15 | 0 | Br | F | H | CF$_3$ | H |
| 16 | 0 | Cl | F | H | CF$_3$ | H |
| 17 | 1 | CH$_3$ | H | H | CH$_2$CH$_3$ | H |
| 18 | 1 | CH$_3$ | F | H | CF$_2$CF$_3$ | H |
| 19 | 1 | CH$_3$ | F | CH$_3$ | CF$_3$ | H |
| 20 | 0 | CH$_3$ | CH$_3$ | H | CH$_3$ | H |
| 21 | 0 | CH$_3$ | H | H | H | CH$_3$ |
| 22 | 0 | CH$_3$ | F | H | CF$_2$CH$_3$ | H |
| 23 | 0 | CH$_3$ | CH$_3$ | H | c-Pr | H |
| 24 | 1 | CH$_3$ | CH$_3$ | H | CH$_2$CH$_3$ | H |
| 25 | 0 | CH$_3$ | H | H | H | H |
| 26 | 1 | CH$_3$ | F | H | CF$_2$CF$_3$ | H |
| 27 | 1 | CH$_3$ | H | H | H | CH$_3$ |
| 28 | 1 | CH$_3$ | H | H | H | H |
| 29 | 1 | Cl | F | H | CF$_3$ | H |
| 30 | 0 | CH$_3$ | CH$_3$ | CH$_3$ | CF$_3$ | H |
| 31 | 0 | CH$_3$ | F | H | i-Pr | H |
| 32 | 0 | CH$_3$ | F | H | CF$_2$H | H |
| 33 | 1 | CH$_3$ | CH$_3$ | H | CF$_2$CF$_3$ | H |
| 34 | 1 | Cl | H | H | CF$_3$ | H |
| 35 | 1 | CH$_3$ | CH$_3$ | H | c-Pr | H |
| 36 | 0 | CH$_3$ | CH$_3$ | H | CF$_2$CF$_3$ | H |
| 37 | 0 | CH$_3$ | F | H | c-Pr | H |
| 39 | 0 | CH$_3$ | CH$_3$ | H | CH$_2$CH$_3$ | H |
| 40 | 1 | CH$_3$ | H | H | H | F |
| 41 | 1 | Br | F | H | CF$_3$ | H |
| 43 | 0 | CH$_3$ | H | H | CH$_2$CH$_3$ | H |
| 44 | 0 | CH$_3$ | F | H | CH$_3$ | H |
| 45 | 1 | CH$_3$ | CH$_3$ | H | CF$_2$CF$_3$ | H |
| 46 | 1 | CH$_3$ | F | H | CH$_3$ | H |
| 47 | 0 | CH$_3$ | H | H | CF$_3$ | H |
| 48 | 1 | CH$_3$ | CH$_3$ | H | CH$_3$ | CH$_3$ |
| 49 | 1 | CH$_3$ | CH$_3$ | H | CF$_3$ | H |
| 50 | 1 | CH$_3$ | H | H | CF$_3$ | H |
| 51 | 0 | CH$_3$ | CH$_3$ | H | CF$_2$CH$_3$ | H |
| 52 | 1 | CH$_3$ | F | H | i-Pr | H |
| 53 | 1 | CH$_3$ | Cl | H | CF$_3$ | H |
| 54 | 0 | Cl | H | H | CF$_3$ | H |
| 55 | 1 | CH$_3$ | F | H | CF$_2$H | H |
| 56 | 1 | CH$_3$ | CH$_3$ | H | CF$_3$ | H |
| 57 | 0 | CH$_3$ | F | H | CH$_2$CH$_3$ | H |
| 58 | 0 | CH$_3$ | F | H | Ph | H |
| 59 | 0 | CH$_3$ | Cl | H | CF$_3$ | H |

Furthermore, the following compounds of the formula (IIa) (cf. Table 2) and of the formula (XXXI) (cf. Table 3) were prepared according to the processes described above.

TABLE 2

Compounds of the formula IIa (IIa) where W = F

| Compound number | Y | X | R$^3$ | R$^6$ | logP (HCOOH) | logP (neutral) |
|---|---|---|---|---|---|---|
| IIa-1 | CH$_3$ | F | CF$_3$ | H | 3.61 | 3.60 |
| IIa-2 | CH$_3$ | CH$_3$ | CF$_3$ | H | 3.63 | 3.61 |
| IIa-3 | Cl | Cl | CF$_3$ | H | 4.24 | 4.13 |
| IIa-4 | Cl | F | CF$_3$ | H | 3.83 | 3.73 |
| IIa-5 | Br | F | CF$_3$ | H | 3.88 | 3.78 |
| IIa-6 | CH$_3$ | H | CF$_3$ | H | 3.58 | 3.49 |
| IIa-7 | Cl | H | CF$_3$ | H | 3.66 | 3.65 |
| IIa-8 | CH$_3$ | Cl | CF$_3$ | H | 4.05 | 3.99 |
| IIa-9 | CH$_3$ | F | CF$_2$H | H | 3.23 | 3.21 |
| IIa-10 | CH$_3$ | CH$_3$ | CF$_2$H | H | 3.24 | 3.15 |
| IIa-11 | CH$_3$ | F | CF$_2$CH$_3$ | H | 3.55 | 3.49 |
| IIa-12 | CH$_3$ | CH$_3$ | CF$_2$CH$_3$ | H | 3.52 | 3.40 |
| IIa-13 | CH$_3$ | F | CF$_2$CH$_3$ | H | 4.09 | 3.88 |
| IIa-14 | CH$_3$ | CH$_3$ | CF$_2$CH$_3$ | H | 4.10 | 3.99 | n.d. = not determined

TABLE 3

Compounds of the formula (XXXI)

(XXXI) where W = F

| Compound number | Y | X | R$^3$ | R$^6$ | logP (HCOOH) | logP (neutral) |
|---|---|---|---|---|---|---|
| XXXI-1 | CH$_3$ | F | CF$_3$ | H | 2.77 | 1.43 |
| XXXI-2 | CH$_3$ | CH$_3$ | CF$_3$ | H | 2.87 | n.d. |
| XXXI-3 | Cl | Cl | CF$_3$ | H | 3.13 | n.d. |
| XXXI-4 | Cl | F | CF$_3$ | H | 2.86 | 1.45 |
| XXXI-5 | Br | F | CF$_3$ | H | 2.93 | n.d. |
| XXXI-6 | CH$_3$ | H | CF$_3$ | H | 2.80 | n.d. |
| XXXI-7 | Cl | H | CF$_3$ | H | 2.84 | n.d. |
| XXXI-8 | CH$_3$ | Cl | CF$_3$ | H | 3.01 | 1.44 |
| XXXI-9 | CH$_3$ | F | CF$_2$H | H | 2.47 | n.d. |
| XXXI-10 | CH$_3$ | CH$_3$ | CF$_2$H | H | 2.53 | n.d. |
| XXXI-11 | CH$_3$ | F | CF$_2$CH$_3$ | H | 2.72 | n.d. |
| XXXI-12 | CH$_3$ | CH$_3$ | CF$_2$CH$_3$ | H | n.d. | n.d. |
| XXXI-13 | CH$_3$ | F | CF$_2$CF$_3$ | H | n.d. | n.d. |
| XXXI-14 | CH$_3$ | CH$_3$ | CF$_2$CF$_3$ | H | n.d. | 1.63 | n.d. = not determined

NMR Peak List Method

The 1H NMR data of selected examples are stated in the form of 1H NMR peak lists. For each signal peak, first the δ value in ppm and then the signal intensity in round brackets are listed. The δ value—signal intensity number pairs for different signal peaks are listed with separation from one another by semicolons.

The peak list for one example therefore takes the form of:
$\delta_1$ (intensity$_1$);$\delta$ (intensity$_2$); . . . ;$\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may, but need not, occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

TABLE 4

NMR data of the compounds according to Table 1:

Example 1: $^1$H-NMR(400.0 MHz, DMSO):
δ = 9.238(0.6); 8.720(4.4); 8.292(0.7); 8.290(0.7); 7.905(2.9); 7.886(3.0); 7.493(2.4); 7.465(2.4); 7.175(4.8); 5.758(0.7); 4.047(1.2); 4.022(4.0); 3.996(4.2); 3.970(1.4); 3.322(24.9); 2.670(0.4); 2.524(1.3); 2.519(2.1); 2.510(23.9); 2.506(47.6); 2.501(62.4); 2.497(44.8); 2.492(21.0); 2.443(16.0); 2.328(0.4); 0.008(0.4); 0.000(10.6)

Example 2: $^1$H-NMR(400.0 MHz, DMSO):
δ = 9.238(0.7); 8.753(4.7); 8.291(0.8); 8.185(3.1); 8.167(3.1); 7.609(2.3); 7.582(2.2); 7.173(5.1); 5.757(4.4); 4.286(0.4); 4.259(0.5); 4.250(0.6); 4.223(0.6); 4.070(0.6); 4.044(0.6); 4.034(0.5); 4.008(0.4); 3.321(27.5); 2.745(0.7); 2.675(0.4); 2.670(0.6); 2.666(0.4); 2.524(1.8); 2.510(33.0); 2.506(64.8); 2.501(84.2); 2.497(60.6); 2.492(29.0); 2.479(16.0); 2.333(0.4); 2.328(0.6); 2.324(0.4); 1.236(0.4); 0.000(0.4)

Example 3: $^1$H-NMR(400.0 MHz, DMSO):
δ = 9.237(0.7); 9.172(0.6); 9.155(1.9); 9.125(0.8); 8.742(2.3); 8.720(9.5); 8.704(0.6); 8.318(4.6); 8.312(4.3); 8.290(1.1); 8.131(2.4); 8.129(2.3); 8.093(13.2); 8.070(16.0); 8.006(0.8); 7.988(0.4); 7.850(0.5); 7.840(0.6); 7.764(0.4); 7.620(0.6); 7.522(0.3); 7.430(0.4); 7.344(0.6); 7.325(0.5); 7.244(11.7); 7.224(0.5); 7.185(0.7); 6.781(0.5); 5.958(0.3); 5.537(0.4); 4.246(0.5); 4.231(1.1); 4.220(1.8); 4.206(3.4); 4.195(3.5); 4.181(3.6); 4.170(3.5); 4.156(1.9); 4.144(1.3); 4.130(0.8); 3.380(0.4); 3.324(311.3); 2.680(2.8); 2.675(5.7); 2.671(7.8); 2.666(5.6); 2.662(2.7); 2.639(0.3); 2.620(0.6); 2.606(0.4); 2.600(0.4); 2.541(4.7); 2.524(21.0); 2.511(436.6); 2.506(875.2); 2.502(1147.4); 2.497(818.8); 2.493(387.3); 2.408(0.4); 2.337(2.6); 2.333(5.5); 2.328(7.5); 2.324(5.4); 1.259(0.4); 1.235(1.3); 0.146(4.7); 0.027(0.3); 0.008(37.7); 0.000(1067.8); −0.009(37.2); −0.030(1.3); −0.054(0.6); −0.068(0.5); −0.087(0.4); −0.092(0.4); −0.150(4.9)

Example 4: $^1$H-NMR(400.0 MHz, DMSO):
δ = 19.997(1.1); 8.714(1.2); 8.663(1.3); 8.316(4.9); 8.303(3.2); 8.290(2.2); 8.269(2.1); 7.224(1.5); 7.210(1.4); 3.323(2222.9); 2.675(11.9); 2.671(16.0); 2.666(11.6); 2.541(10.5); 2.524(46.3); 2.510(902.8); 2.506(1775.9); 2.501(2306.4); 2.497(1634.6); 2.493(766.6); 2.333(10.8); 2.328(14.7); 2.324(10.5); 1.234(2.8); 0.838(0.7); 0.146(15.4); 0.008(154.0); 0.000(3106.4); −0.009(92.9); −0.150(13.7)

Example 5: $^1$H-NMR(400.0 MHz, DMSO):
δ = 8.588(4.6); 8.316(0.4); 7.641(5.6); 7.328(4.3); 7.126(5.0); 5.756(0.5); 4.031(1.2); 4.005(3.9); 3.979(4.0); 3.953(1.4); 3.321(66.0); 2.675(0.9); 2.670(1.3); 2.666(0.9); 2.662(0.5); 2.541(0.9); 2.524(3.2); 2.510(68.6); 2.506(139.2); 2.501(183.6); 2.497(131.5); 2.492(62.1); 2.380(15.2); 2.337(0.4); 2.333(0.9); 2.328(1.2); 2.324(0.9); 2.319(0.4); 2.041(16.0); 0.146(0.8); 0.008(6.8); 0.000(196.8); −0.009(6.8); −0.150(0.8)

Example 6: $^1$H-NMR(400.0 MHz, DMSO):
δ = 20.011(0.5); 8.637(1.5); 8.620(2.1); 8.316(4.9); 7.918(3.2); 7.464(1.4); 7.439(2.0); 7.131(3.1); 5.756(0.4); 4.300(0.5); 4.271(0.5); 4.263(0.5); 4.235(0.5); 4.129(0.8); 4.103(0.7); 4.081(0.8); 4.055(0.7); 4.018(0.5); 3.976(0.5); 3.945(0.5); 3.919(0.5); 3.883(0.6); 3.399(1.1); 3.391(1.2); 3.323(2085.6); 3.268(0.5); 2.980(0.4); 2.937(0.5); 2.675(12.0); 2.671(16.0); 2.666(11.5); 2.541(11.4); 2.524(49.6); 2.510(913.2); 2.506(1787.3); 2.502(2314.4); 2.497(1649.1); 2.493(779.4); 2.428(10.1); 2.337(5.2); 2.333(10.7); 2.328(14.5); 2.324(10.4); 2.153(7.3); 2.145(5.1); 1.235(1.6); 0.146(14.5); 0.116(0.6); 0.077(1.1); 0.069(1.0); 0.059(1.1); 0.008(138.4); 0.000(3114.1); −0.009(108.4); −0.056(0.6); −0.150(14.2)

Example 7: $^1$H-NMR(400.0 MHz, DMSO):
δ = 8.372 (5.6); 8.009 (3.2); 7.991 (3.2); 7.560 (2.5); 7.533 (2.5); 6.493 (6.1); 6.492 (5.9); 5.757 (7.9); 4.255 (0.5); 4.247 (0.4); 4.228 (0.6); 4.219 (0.9); 4.192 (0.8); 4.165 (0.3); 4.115 (1.0); 4.106 (0.4); 4.088 (1.1); 4.078 (0.7); 4.060 (0.4); 4.051 (0.7); 3.329 (25.0); 2.506 (26.1); 2.502 (33.7); 2.497 (24.9); 2.464 (16.0); 2.411 (0.5); 2.329 (0.3); 2.012 (0.3); 1.996 (1.0); 1.980 (1.5); 1.964 (1.1); 1.948 (0.4); 1.030 (0.4); 1.007 (10.9); 0.993 (5.3); 0.988 (5.4); 0.000 (6.4)

TABLE 4-continued

NMR data of the compounds according to Table 1:

Example 8: $^1$H-NMR(400.0 MHz, DMSO):
δ = 7.895 (2.5); 7.876 (2.5); 7.519 (2.2); 7.492 (2.2); 7.058 (4.9); 4.063 (0.4); 4.049 (0.5); 4.037 (0.5); 4.023 (1.7); 3.997 (2.4); 3.970 (1.7); 3.957 (0.5); 3.944 (0.5); 3.931 (0.4); 3.333 (20.7); 2.671 (0.4); 2.525 (1.1); 2.511 (23.8); 2.507 (47.9); 2.502 (62.7); 2.498 (46.0); 2.493 (22.8); 2.444 (14.2); 2.375 (1.0); 2.329 (0.4); 2.212 (16.0); 0.146 (0.4); 0.008 (3.0); 0.000 (83.1); −0.009 (3.3); −0.150 (0.4)

Example 9: $^1$H-NMR(400.0 MHz, DMSO):
δ = 8.734 (4.9); 7.923 (2.9); 7.905 (2.9); 7.495 (2.5); 7.468 (2.5); 7.228 (5.6); 7.226 (5.7); 4.050 (1.2); 4.024 (3.9); 3.998 (4.1); 3.973 (1.4); 3.322 (31.9); 2.675 (0.4); 2.671 (0.5); 2.666 (0.4); 2.524 (1.3); 2.510 (29.4); 2.506 (59.6); 2.502 (79.5); 2.497 (59.1); 2.493 (29.8); 2.445 (16.0); 2.333 (0.4); 2.328 (0.5); 2.324 (0.4); 0.008 (0.3); 0.000 (10.2); −0.008 (0.4)

Example 10: $^1$H-NMR(400.0 MHz, DMSO):
δ = 8.446 (4.8); 8.413 (0.4); 8.316 (0.9); 8.029 (2.8); 8.011 (2.8); 7.569 (2.2); 7.542 (2.2); 6.389 (4.3); 6.387 (4.3); 4.260 (0.5); 4.251 (0.3); 4.233 (0.6); 4.224 (0.8); 4.196 (0.8); 4.128 (0.9); 4.101 (1.0); 4.091 (0.7); 4.074 (0.4); 4.064 (0.6); 3.322 (149.5); 2.730 (1.1); 2.675 (1.4); 2.671 (1.9); 2.666 (1.4); 2.586 (1.3); 2.567 (3.8); 2.548 (4.2); 2.524 (5.3); 2.510 (104.6); 2.506 (208.9); 2.502 (276.9); 2.497 (208.3); 2.470 (16.0); 2.333 (1.4); 2.328 (2.1); 2.324 (1.5); 1.235 (0.4); 1.217 (5.4); 1.198 (11.4);1.179 (5.2); 0.146 (1.2); 0.008 (10.9); 0.000 (280.5); −0.008 (14.3); −0.150 (1.3)

Example 11: $^1$H-NMR(400.0 MHz, DMSO):
δ = 8.645 (13.2); 8.316 (0.4); 8.167 (0.9); 8.157 (6.6); 8.152 (7.7); 8.144 (7.2); 8.141 (6.1); 8.133(7.5); 8.121 (8.0); 8.103 (7.6); 7.603 (5.8); 7.576 (5.8); 7.560 (2.1); 7.550 (16.0); 7.545 (14.9); 7.537 (9.2); 7.533 (9.0); 7.523 (2.4); 7.509 (0.6); 7.157 (14.4); 7.155 (13.7); 5.756 (10.1); 4.312 (0.4); 4.285 (1.3); 4.276 (0.8); 4.258 (1.6); 4.249 (2.1); 4.230 (0.8); 4.221 (2.1); 4.194 (0.7); 4.169 (0.6); 4.142 (2.1); 4.115 (2.3); 4.106 (1.6); 4.088 (1.0); 4.079 (1.4); 4.052 (0.5); 3.325 (90.4); 2.676 (0.6); 2.671 (0.8); 2.666 (0.6); 2.524 (2.5); 2.511 (46.0); 2.506 (91.8); 2.502 (120.2); 2.497 (88.0); 2.492 (56.7); 2.333 (0.7); 2.329 (1.0); 2.324 (0.7); 0.146 (0.8); 0.008 (7.3); 0.000 (188.1); −0.009 (6.7); −0.150 (0.8)

Example 12: $^1$H-NMR(400.0 MHz, DMSO):
δ = 8.339 (6.7); 8.191 (3.5); 8.184 (3.4); 7.704 (3.5); 7.700 (3.5); 7.445 (2.2); 7.425 (3.3); 7.353 (2.3); 7.349 (2.2); 7.333 (1.5); 7.328 (1.4); 5.757 (1.0); 4.106 (1.3); 4.080 (3.9); 4.054 (4.0); 4.029 (1.3); 3.324 (49.3); 2.670 (0.6); 2.502 (92.9); 2.403 (16.0); 2.328 (0.6); 1.235 (0.7); 0.000 (5.1)

Example 13: $^1$H-NMR(400.0 MHz, DMSO):
δ = 8.089 (5.3); 7.990 (0.4); 7.489 (5.6); 7.293 (4.3); 6.792 (0.4); 5.758 (0.4); 4.752 (0.3); 4.037 (0.8); 4.035 (0.8); 4.012 (2.4); 4.009 (2.4); 3.986 (2.4); 3.983 (2.5); 3.960 (0.9); 3.957 (0.9); 3.694 (0.4); 3.668 (0.4); 3.337 (15.5); 3.336 (16.9); 3.330 (19.8); 2.525 (0.5); 2.520 (0.7); 2.511 (11.3); 2.507 (23.2); 2.502 (30.8); 2.498 (22.6); 2.493 (11.3); 2.372 (15.1); 2.346 (0.6); 2.338 (1.2); 2.329 (0.4); 2.291 (12.6); 2.204 (1.5); 2.154 (0.3); 2.145 (1.1); 2.055 (0.5); 1.998 (14.2); 1.989 (16.0); 1.949 (0.4); 0.987 (0.4); 0.969 (0.6); 0.008 (1.1); 0.000 (33.6); −0.009 (1.3)

Example 14: $^1$H-NMR(400.0 MHz, DMSO):
δ = 9.266 (0.3); 8.317 (0.9); 7.910 (3.2); 7.901 (2.2); 7.485 (2.3); 7.474 (1.5); 7.189 (0.5); 7.013 (1.9); 6.999 (2.8); 4.310 (0.5); 4.282 (0.5); 4.273 (0.6); 4.246 (0.6); 4.219 (0.3); 4.193 (0.6); 4.184 (0.6); 4.166 (0.6); 4.157 (0.6); 3.913 (0.5); 3.886 (0.6); 3.876 (0.5); 3.859 (0.3); 3.849 (0.5); 3.331 (519.1); 2.676 (1.9); 2.671 (2.7); 2.667 (1.9); 2.662 (1.0); 2.524 (6.0); 2.520 (9.8); 2.511 (146.3); 2.507 (304.5); 2.502 (406.6); 2.498 (299.7); 2.493 (148.9); 2.435 (8.0); 2.424 (5.5); 2.375 (0.5); 2.338 (1.0); 2.333 (2.0); 2.329 (2.8); 2.324 (2.2); 2.296 (1.6); 2.267 (0.5); 2.253 (1.8); 2.180 (6.0); 2.109 (0.6); 2.091 (16.0); 1.351 (0.8); 1.259 (0.4); 1.233 (1.0); 0.008 (1.3); 0.000 (44.6); −0.008 (1.8)

Example 15: $^1$H-NMR(400.0 MHz, DMSO):
δ = 8.723 (10.3); 8.316 (0.5); 8.045 (9.4); 8.040 (7.0); 8.022 (16.0); 7.211 (11.1); 5.756 (2.5); 4.184 (2.2); 4.159 (7.0); 4.146 (0.8); 4.133 (7.3); 4.108 (2.5); 3.324 (132.3); 2.680 (0.4); 2.675 (0.7); 2.671 (1.1); 2.666 (0.8); 2.662 (0.3); 2.524 (2.6); 2.519 (4.1); 2.511 (58.1); 2.506 (118.2); 2.502 (156.8); 2.497 (112.2); 2.493 (52.3); 2.338 (0.4); 2.333 (0.8); 2.328 (1.1); 2.324 (0.8); 2.319 (0.3); 1.235 (0.5); 0.146 (0.7); 0.008 (5.7); 0.000 (174.4); −0.009 (5.5); −0.150 (0.7)

Example 16: $^1$H-NMR(400.0 MHz, DMSO):
δ = 10.306 (0.5); 8.725 (14.9); 8.597 (0.3); 8.405 (0.4); 8.316 (0.7); 8.117 (0.4); 8.087 (9.3); 8.069 (9.3); 7.945 (10.8); 7.921 (10.8); 7.698 (0.5); 7.672 (0.5); 7.214 (16.0); 5.757 (2.3); 4.184 (3.3); 4.159 (10.5); 4.134 (10.9); 4.108 (3.7); 3.970 (0.6); 3.943 (0.7); 3.918 (0.4); 3.640 (0.4); 3.326 (311.9); 3.295 (0.5); 3.256 (0.4); 3.142 (0.3); 2.675 (1.5); 2.671 (2.0); 2.666 (1.5); 2.541 (0.8); 2.524 (5.6); 2.510 (118.1); 2.506 (232.8); 2.502 (304.3); 2.497 (223.3); 2.493 (110.3); 2.333 (1.5); 2.328 (2.0); 2.324 (1.5); 1.178 (0.7); 1.160 (1.4); 1.143 (0.8); 0.008 (0.8); 0.000 (23.5); −0.009 (0.9)

Example 17: $^1$H-NMR(400.0 MHz, DMSO):
δ = 8.431 (5.6); 8.317 (0.7); 7.891 (3.6); 7.885 (3.8); 7.640 (1.6); 7.635 (1.6); 7.620 (2.5); 7.614 (2.4); 7.536 (3.2); 7.515 (2.2); 6.368 (4.8); 5.757 (0.3); 4.234 (0.8); 4.224 (0.5); 4.206 (0.9); 4.197 (1.3); 4.178 (0.4); 4.169 (1.3); 4.142 (0.5); 4.114 (0.4); 4.086 (1.3); 4.060 (1.4); 4.050 (0.9); 4.033 (0.5); 4.023 (0.8); 3.325 (406.6); 2.675 (2.6); 2.671 (3.5); 2.666 (2.6); 2.575 (1.8); 2.556 (4.7); 2.537 (5.8); 2.524 (9.7); 2.510 (199.9); 2.506 (396.5); 2.502 (519.5); 2.497 (385.0); 2.493 (194.5); 2.444 (16.0); 2.388 (0.7); 2.333 (2.4); 2.328 (3.3); 2.324 (2.5); 1.236 (0.6); 1.216 (6.1); 1.198 (12.8); 1.179 (5.8); 0.008 (1.6); 0.000 (41.2); −0.008 (1.5)

Example 18: $^1$H-NMR(400.0 MHz, DMSO):
δ = 8.668 (9.3); 8.627 (0.8); 8.323 (0.8); 8.304 (0.4); 8.148 (5.4); 8.129 (5.5); 7.768 (0.4); 7.742 (0.4); 7.608 (4.6); 7.581 (4.6); 6.793 (10.6); 4.991 (0.5); 4.966 (0.6); 4.287 (1.0); 4.252 (1.6); 4.224 (1.4); 4.196 (0.5); 4.124 (0.5); 4.098 (1.5); 4.072 (1.7); 4.062 (1.4); 4.044 (0.9); 4.035 (1.2); 4.009 (0.4); 3.330 (113.6); 2.750 (2.3); 2.679 (1.5); 2.510 (240.7); 2.488 (38.4); 2.337 (1.6); 2.003 (7.4); 1.955 (16.0); 1.907 (8.3); 1.245 (0.3); 0.008 (0.5)

TABLE 4-continued

NMR data of the compounds according to Table 1:

Example 19: ¹H-NMR(400.0 MHz, DMSO):
δ = 20.012 (0.4); 8.317 (2.9); 8.187 (2.7); 8.177 (1.9); 8.169 (2.9); 8.159 (1.7); 7.652 (2.2); 7.644 (1.4); 7.626 (2.2); 7.617 (1.4); 7.054 (3.1); 7.047 (5.1); 4.385 (0.8); 4.376 (0.4); 4.358 (0.9); 4.349 (1.0); 4.321 (1.1); 4.294 (0.4); 4.285 (0.4); 4.258 (0.4); 4.248 (0.8); 4.221 (0.8); 4.200 (0.8); 4.173 (0.9); 4.135 (0.4); 3.978 (0.4); 3.952 (1.1); 3.925 (1.1); 3.915 (0.9); 3.899 (0.5); 3.888 (1.0); 3.861 (0.3); 3.330 (1595.1); 2.676 (5.4); 2.671 (7.6); 2.667 (5.6); 2.524 (18.0); 2.511 (415.9); 2.507 (858.2); 2.502 (1139.8); 2.498 (837.1); 2.493 (412.0); 2.481 (24.3); 2.475 (14.3); 2.333 (5.5); 2.329 (7.6); 2.324 (6.3); 2.276 (9.6); 2.192 (16.0); 1.351 (1.7); 1.298 (0.6); 1.258 (1.0); 1.233 (2.6); 1.161 (0.7); 1.094 (0.4); 0.853 (0.4); 0.146 (0.6); 0.008 (4.2); 0.000 (127.6); −0.008 (4.2); −0.150 (0.6)
Example 20: ¹H-NMR(601.6 MHz, DMSO):
δ = 19.975 (0.5); 9.713 (0.4); 9.694 (0.4); 9.573 (1.4); 8.411 (1.7); 8.393 (1.6); 8.316 (0.6); 8.270 (3.8); 8.267 (3.8); 8.227 (1.1); 7.931 (5.2); 7.508 (1.1); 7.358 (2.2); 7.293 (0.9); 7.133 (4.1); 7.112 (1.8); 6.375 (1.0); 4.017 (0.5); 3.999 (1.6); 3.982 (1.6); 3.965 (0.6); 3.796 (1.2); 3.778 (3.6); 3.761 (3.8); 3.744 (1.3); 3.326 (96.7); 2.614 (0.9); 2.523 (1.5); 2.520 (1.9); 2.517 (1.9); 2.508 (56.6); 2.505 (124.1); 2.502 (171.8); 2.499 (122.8); 2.496 (55.0); 2.386 (1.0); 2.370 (3.3); 2.330 (15.7); 2.289 (6.9); 2.271 (3.0); 2.178 (7.7); 2.173 (16.0); 2.000 (3.3); 1.351 (1.6); 1.336 (0.6); 1.259 (0.5); 1.249 (0.8); 1.228 (1.1); 0.000 (1.9)
Example 21: ¹H-NMR(400.0 MHz, DMSO):
δ = 8.278 (5.3); 7.905 (3.6); 7.639 (3.2); 7.634 (3.4); 7.414 (2.3); 7.393 (3.1); 7.291 (2.2); 7.286 (2.1); 7.271 (1.6); 7.266 (1.6); 4.111 (1.3); 4.085 (3.9); 4.059 (4.1); 4.034 (1.4); 3.325 (43.6); 2.671 (0.6); 2.666 (0.5); 2.506 (67.0); 2.502 (88.0); 2.497 (66.3); 2.397 (16.0); 2.333 (0.5); 2.328 (0.6); 2.324 (0.4); 1.998 (13.7); 1.235 (0.5); 0.000 (9.6); −0.008 (0.4)
Example 22: ¹H-NMR(400.0 MHz, DMSO):
δ = 8.618 (4.7); 7.885 (2.9); 7.867 (2.9); 7.475 (2.6); 7.448 (2.5); 6.779 (5.4); 4.062 (1.2); 4.037 (3.9); 4.011 (4.1); 3.985 (1.4); 3.322 (44.2); 2.675 (0.4); 2.671 (0.6); 2.666 (0.4); 2.524 (1.4); 2.506 (65.8); 2.502 (88.0); 2.497 (66.2); 2.435 (16.0); 2.333 (0.4); 2.328 (0.6); 2.324 (0.5); 1.997 (4.1); 1.949 (8.9); 1.900 (4.7); 0.008 (0.3); 0.000 (10.4); −0.008 (0.5)
Example 23: ¹H-NMR(601.6 MHz, DMSO):
δ = 8.182 (5.5); 7.500 (5.5); 7.281 (4.3); 6.446 (5.7); 5.755 (0.4); 4.026 (0.6); 4.012 (1.7); 4.009 (1.8); 3.995 (1.8); 3.992 (1.9); 3.974 (0.7); 3.326 (57.8); 2.613 (0.5); 2.523 (0.8); 2.520 (1.0); 2.517 (1.0); 2.508 (29.7); 2.505 (65.1); 2.502 (90.5); 2.499 (65.5); 2.496 (30.2); 2.391 (0.5); 2.386 (0.5); 2.361 (15.5); 2.086 (0.7); 2.065 (0.4); 1.994 (16.0); 1.973 (0.8); 1.963 (1.3); 1.954 (0.8); 1.950 (0.8); 1.941 (0.4); 1.398 (0.8); 0.991 (3.7); 0.987 (6.0); 0.974 (3.2); 0.000 (1.0)
Example 24: ¹H-NMR(400.0 MHz, DMSO):
δ = 8.323 (7.3); 8.305 (0.5); 7.838 (0.4); 7.749 (4.8); 7.736 (3.4); 7.578 (0.4); 7.436 (2.5); 7.416 (3.6); 6.374 (4.0); 6.368 (3.3); 4.269 (0.5); 4.241 (0.5); 4.232 (0.6); 4.205 (0.4); 4.151 (0.9); 4.125 (2.7); 4.098 (2.9); 4.071 (1.0); 4.025 (0.7); 3.998 (0.7); 3.988 (0.5); 3.961 (0.5); 3.321 (216.3); 2.680 (2.0); 2.675 (2.4); 2.671 (3.1); 2.594 (1.3); 2.576 (3.8); 2.558 (4.0); 2.553 (3.5); 2.538 (2.3); 2.506 (357.6); 2.501 (466.5); 2.497 (362.9); 2.418 (16.0); 2.355 (0.3); 2.328 (3.1); 2.324 (2.5); 2.294 (0.4); 2.261 (0.4); 2.139 (1.3); 2.116 (13.5); 2.110 (10.6); 1.227 (4.6); 1.222 (4.0); 1.208 (9.4); 1.204 (7.8); 1.190 (4.6); 1.185 (3.8); 0.146 (2.7); 0.008 (26.2); 0.000 (549.3); −0.060 (0.4); −0.150 (2.8)
Example 25: ¹H-NMR(400.0 MHz, DMSO):
δ = 8.410 (5.2); 8.317 (0.4); 7.998 (3.4); 7.981 (3.5); 7.649 (3.2); 7.644 (3.3); 7.418 (2.2); 7.397 (3.0); 7.301 (2.2); 7.295 (2.2); 7.281 (1.6); 7.275 (1.6); 6.524 (2.8); 6.522 (3.0); 6.507 (2.8); 6.505 (2.9); 4.117 (1.3); 4.091 (4.1); 4.065 (4.3); 4.039 (1.5); 3.323 (115.5); 2.675 (1.3); 2.671 (1.6); 2.666 (1.2); 2.524 (4.1); 2.519 (6.1); 2.510 (86.0); 2.506 (177.4); 2.501 (236.9); 2.497 (175.3); 2.493 (87.2); 2.395 (16.0); 2.333 (1.1); 2.328 (1.5); 2.324 (1.1); 1.989 (0.6); 1.175 (0.3); 0.146 (0.9); 0.008 (6.7); 0.000 (210.8); −0.009 (7.6); −0.150 (0.9)
Example 26: ¹H-NMR(400.0 MHz, DMSO):
δ = 8.763 (13.6); 8.719 (1.6); 8.401 (0.9); 8.382 (0.9); 8.324 (1.0); 8.227 (8.0); 8.209 (8.1); 7.782 (0.8); 7.755 (0.7); 7.617 (6.3); 7.590 (6.3); 7.222 (16.0); 5.764 (2.6); 5.022 (0.3); 4.997 (1.1); 4.972 (1.2); 4.948 (0.4); 4.323 (0.4); 4.295 (1.3); 4.260 (1.9); 4.232 (1.7); 4.206 (0.6); 4.099 (0.6); 4.071 (1.6); 4.044 (1.9); 4.008 (1.3); 3.982 (0.5); 3.331 (223.5); 2.753 (5.0); 2.683 (2.7); 2.679 (3.5); 2.675 (2.8); 2.647 (0.4); 2.514 (411.2); 2.510 (530.6); 2.506 (403.1); 2.488 (54.5); 2.341 (2.6); 2.337 (3.4); 2.332 (2.7); 1.243 (0.5); 1.223 (0.4); 1.192 (0.5); 1.182 (0.3); 0.008 (1.2)
Example 27: ¹H-NMR(400.0 MHz, DMSO):
δ = 8.368 (5.6); 7.924 (3.6); 7.922 (3.7); 7.901 (3.7); 7.895 (3.9); 7.652 (1.7); 7.646 (1.6); 7.631 (2.4); 7.626 (2.4); 7.542 (3.2); 7.521 (2.2); 4.238 (0.9); 4.228 (0.5); 4.211 (1.0); 4.201 (1.4); 4.183 (0.4); 4.174 (1.3); 4.147 (0.4); 4.113 (0.4); 4.086 (1.3); 4.076 (0.3); 4.059 (1.4); 4.049 (0.9); 4.032 (0.5); 4.022 (0.9); 3.325 (76.1); 2.671 (0.6); 2.666 (0.4); 2.524 (1.4); 2.510 (27.8); 2.506 (56.4); 2.501 (76.0); 2.497 (58.1); 2.493 (30.0); 2.447 (16.0); 2.333 (0.3); 2.328 (0.5); 2.324 (0.4); 2.010 (13.7); 1.351 (0.4); 1.298 (0.6); 1.259 (0.8); 1.250 (0.5); 1.234 (1.2); 0.000 (0.5)
Example 28: ¹H-NMR(400.0 MHz, DMSO):
δ = 8.498 (5.4); 8.016 (3.8); 7.999 (3.9); 7.914 (3.6); 7.909 (3.8); 7.659 (1.7); 7.653 (1.6); 7.638 (2.4); 7.633 (2.3); 7.546 (3.1); 7.525 (2.2); 6.553 (3.0); 6.551 (3.3); 6.537 (2.9); 6.534 (3.1); 4.236 (0.8); 4.226 (0.5); 4.209 (0.9); 4.199 (1.3); 4.181 (0.4); 4.172 (1.3); 4.144 (0.4); 4.119 (0.4); 4.092 (1.3); 4.082 (0.3); 4.065 (1.5); 4.055 (0.9); 4.038 (0.5); 4.028 (0.9); 3.345 (133.3); 3.341 (137.3); 3.290 (0.3); 2.671 (0.5); 2.667 (0.3); 2.525 (1.2); 2.520 (1.8); 2.511 (26.1); 2.507 (53.8); 2.502 (71.6); 2.498 (52.4); 2.493 (25.4); 2.448 (16.0); 2.333 (0.3); 2.329 (0.5); 2.324 (0.3); 0.008 (1.9); 0.000 (59.6); −0.009 (2.0)
Example 29: ¹H-NMR(400.0 MHz, DMSO):
δ = 8.736 (14.4); 8.316 (2.3); 8.294 (10.4); 8.276 (10.4); 8.122 (9.5); 8.099 (9.5); 7.821 (0.4); 7.197 (16.0); 5.756 (2.4); 4.421 (0.4); 4.392 (1.1); 4.357 (1.7); 4.330 (1.5); 4.302 (0.6); 4.198 (0.9); 4.172 (2.5); 4.162 (1.1); 4.145 (2.9); 4.136 (2.2); 4.118 (1.3); 4.109 (2.0); 4.081 (0.8); 3.323 (659.7); 2.675 (3.6); 2.671 (4.8); 2.666 (3.7); 2.586 (0.4); 2.524 (12.2); 2.510 (278.7); 2.506 (554.9); 2.502 (731.6); 2.497 (544.7); 2.333 (3.6); 2.328 (4.9); 2.324 (3.7); 1.235 (0.8); 1.215 (0.4); 1.184 (0.7); 1.167 (0.9); 1.151 (0.6); 0.146 (0.7); 0.008 (5.6); 0.000 (164.4); −0.008 (7.6); −0.150 (0.8)

TABLE 4-continued

NMR data of the compounds according to Table 1:

Example 30: $^1$H-NMR(400.0 MHz, DMSO):
δ = 7.631 (4.9); 7.463 (0.3); 7.346 (3.9); 7.114 (0.6); 7.005 (4.8); 4.070 (0.5); 4.056 (0.4); 4.045 (0.6); 4.031 (1.2); 4.006 (1.4); 3.983 (1.3); 3.958 (1.3); 3.944 (0.6); 3.932 (0.5); 3.918 (0.6); 3.796 (0.5); 3.769 (0.5); 3.330 (35.4); 2.675 (0.4); 2.671 (0.6); 2.666 (0.4); 2.524 (1.3); 2.520 (2.1); 2.511 (32.6); 2.506 (68.1); 2.502 (92.3); 2.497 (69.3); 2.493 (35.0); 2.375 (13.3); 2.345 (0.6); 2.330 (2.5); 2.182 (0.4); 2.158 (2.4); 2.109 (16.0); 1.985 (13.8); 0.008 (1.6); 0.000 (53.8); −0.009 (2.0)

Example 31: $^1$H-NMR(400.0 MHz, DMSO):
δ = 8.403 (4.2); 7.819 (2.3); 7.800 (2.3); 7.439 (2.0); 7.412 (2.0); 6.353 (4.5); 4.078 (1.0); 4.053 (3.2); 4.027 (3.3); 4.001 (1.1); 3.338 (3.0); 3.333 (9.2); 2.818 (0.4); 2.801 (1.0); 2.783 (1.4); 2.766 (1.1); 2.749 (0.4); 2.511 (3.6); 2.507 (7.4); 2.503 (9.8); 2.498 (7.3); 2.494 (3.8); 2.425 (11.8); 2.400 (0.4); 2.383 (0.7); 2.244 (0.7); 1.397 (1.1); 1.213 (16.0); 1.195 (15.5); 0.984 (0.4); 0.000 (9.2); −0.008 (0.4)

Example 32: $^1$H-NMR(400.0 MHz, DMSO):
δ = 8.622 (4.9); 7.887 (2.9); 7.868 (2.9); 7.475 (2.5); 7.448 (2.5); 6.982 (1.4); 6.847 (7.9); 6.712 (1.6); 5.756 (1.9); 4.056 (1.3); 4.030 (3.9); 4.005 (4.1); 3.979 (1.4); 3.323 (47.5); 2.675 (0.3); 2.671 (0.5); 2.666 (0.4); 2.524 (1.1); 2.510 (27.2); 2.506 (56.2); 2.502 (75.5); 2.497 (56.6); 2.493 (28.9); 2.457 (0.5); 2.437 (16.0); 2.333 (0.4); 2.328 (0.5); 2.324 (0.4); 2.086 (1.3); 0.008 (0.4); 0.000 (11.8); −0.008 (0.5)

Example 33: $^1$H-NMR(400.0 MHz, DMSO):
δ = 8.650 (2.6); 8.627 (3.9); 8.414 (0.3); 8.317 (0.7); 8.098 (0.4); 7.958 (3.9); 7.954 (5.4); 7.549 (0.4); 7.465 (2.4); 7.439 (3.5); 7.172 (6.7); 7.162 (0.4); 5.757 (1.0); 4.303 (0.5); 4.276 (0.6); 4.266 (0.7); 4.239 (0.7); 4.232 (0.3); 4.214 (0.4); 4.167 (0.6); 4.156 (0.5); 4.140 (0.7); 4.130 (1.1); 4.103 (1.2); 4.081 (1.1); 4.054 (1.2); 4.045 (0.6); 4.027 (0.5); 4.018 (0.6); 3.940 (0.6); 3.914 (0.7); 3.904 (0.6); 3.877 (0.5); 3.331 (446.6); 2.692 (0.9); 2.676 (1.5); 2.671 (2.1); 2.666 (1.5); 2.591 (1.1); 2.524 (5.0); 2.511 (114.9); 2.507 (234.5); 2.502 (309.1); 2.498 (226.9); 2.493 (111.8); 2.428 (16.0); 2.333 (1.6); 2.329 (2.2); 2.324 (1.7); 2.173 (1.0); 2.153 (12.5); 2.143 (8.7); 1.351 (0.6); 1.310 (0.4); 1.293 (0.5); 1.259 (0.4); 1.234 (0.9); 1.184 (0.4); 1.175 (0.3); 0.008 (1.1); 0.000 (36.2); −0.008 (1.4)

Example 34: $^1$H-NMR(400.0 MHz, DMSO):
δ = 8.703 (12.7); 8.316 (1.1); 8.100 (10.6); 8.094 (10.9); 7.905 (5.5); 7.884 (16.0); 7.866 (10.0); 7.861 (9.1); 7.845 (3.3); 7.839 (3.5); 7.137 (13.3); 4.394 (0.7); 4.367 (2.5); 4.357 (1.2); 4.340 (2.8); 4.330 (3.5); 4.313 (1.1); 4.303 (3.6); 4.276 (1.1); 4.165 (0.9); 4.139 (3.3); 4.129 (0.9); 4.112 (3.7); 4.102 (2.7); 4.085 (1.4); 4.075 (2.7); 4.048 (0.9); 3.325 (469.0); 3.303 (1.1); 2.679 (0.8); 2.675 (1.6); 2.671 (2.2); 2.666 (1.6); 2.661 (0.8); 2.524 (5.7); 2.511 (122.2); 2.506 (248.6); 2.502 (330.0); 2.497 (238.1); 2.493 (113.6); 2.337 (0.8); 2.333 (1.6); 2.328 (2.2); 2.324 (1.6); 1.235 (0.4); 0.146 (2.2); 0.026 (0.5); 0.019 (1.1); 0.008 (18.3); 0.000 (502.6); −0.009 (18.2); −0.023 (0.9); −0.032 (0.4); −0.150 (2.2)

Example 35: $^1$H-NMR(400.0 MHz, DMSO):
δ = 8.317 (0.7); 8.251 (4.6); 7.731 (4.5); 7.715 (3.1); 7.426 (2.2); 7.406 (3.1); 6.480 (4.1); 6.479 (4.3); 6.474 (3.3); 6.472 (3.1); 4.264 (0.4); 4.237 (0.5); 4.228 (0.6); 4.201 (0.6); 4.141 (0.7); 4.114 (2.4); 4.087 (2.5); 4.060 (0.9); 4.023 (0.6); 3.996 (0.6); 3.986 (0.5); 3.959 (0.5); 3.362 (0.5); 3.330 (358.6); 2.675 (2.0); 2.671 (2.5); 2.667 (1.6); 2.524 (4.8); 2.520 (8.0); 2.511 (118.7); 2.507 (244.5); 2.502 (323.9); 2.498 (237.1); 2.493 (116.6); 2.436 (0.6); 2.412 (16.0); 2.333 (1.6); 2.329 (2.2); 2.324 (1.7); 2.133 (0.8); 2.110 (11.5); 2.102 (8.4); 1.997 (0.8); 1.983 (1.2); 1.976 (1.2); 1.967 (0.9); 1.351 (0.6); 1.259 (0.4); 1.232 (0.9); 1.025 (0.8); 1.004 (6.4); 1.000 (5.5); 0.991 (4.8); 0.988 (4.4); 0.980 (2.8); 0.008 (1.1); 0.000 (38.4); −0.009 (1.4)

Example 36: $^1$H-NMR(400.0 MHz, DMSO):
δ = 8.611 (5.0); 7.663 (5.8); 7.333 (4.5); 7.177 (5.7); 7.175 (5.7); 5.757 (1.1); 4.037 (1.2); 4.011 (3.9); 3.985 (4.0); 3.959 (1.4); 3.346 (5.5); 2.525 (0.5); 2.520 (0.8); 2.511 (12.0); 2.507 (24.8); 2.502 (33.0); 2.498 (24.4); 2.493 (12.1); 2.470 (0.8); 2.411 (0.8); 2.383 (15.2); 2.329 (0.7); 2.199 (0.4); 2.038 (16.0); 1.293 (0.4); 0.000 (8.6)

Example 37: $^1$H-NMR(600.1 MHz, CD$_3$CN):
δ = 8.110 (0.3); 8.106 (0.3); 8.012 (3.8); 7.598 (2.5); 7.586 (2.5); 7.499 (0.3); 7.486 (0.3); 7.264 (2.1); 7.246 (2.1); 6.357 (4.7); 6.355 (4.5); 3.716 (0.8); 3.704 (0.6); 3.629 (1.6); 3.625 (0.4); 3.612 (4.9); 3.608 (1.0); 3.596 (5.0); 3.592 (1.0); 3.579 (1.7); 3.575 (0.4); 3.550 (0.3); 2.499 (16.0); 2.465 (0.9); 2.456 (2.3); 2.411 (0.4); 2.133 (4.3); 1.955 (0.4); 1.951 (0.6); 1.947 (4.5); 1.943 (8.1); 1.939 (11.9); 1.935 (8.0); 1.931 (4.0); 1.914 (0.4); 1.906 (0.7); 1.900 (0.8); 1.893 (1.3); 1.885 (0.8); 1.879 (0.8); 1.871 (0.4); 1.077 (0.5); 1.055 (0.6); 1.042 (1.8); 1.034 (2.2); 1.030 (3.3); 1.026 (2.6); 1.022 (2.9); 1.017 (1.3); 1.012 (0.7); 1.005 (1.7); 1.000 (2.9); 0.995 (2.2); 0.991 (1.4); 0.986 (3.1); 0.982 (1.7); 0.976 (0.6); 0.974 (0.6); 0.000 (1.2)

Example 39: $^1$H-NMR(400.0 MHz, DMSO):
δ = 8.250 (5.3); 7.517 (5.6); 7.293 (4.5); 6.345 (4.6); 6.343 (4.7); 5.755 (4.4); 4.048 (1.0); 4.023 (3.2); 3.997 (3.3); 3.971 (1.1); 3.321 (17.3); 2.579 (1.3); 2.561 (3.8); 2.542 (4.0); 2.523 (2.0); 2.510 (14.4); 2.506 (29.9); 2.501 (40.7); 2.497 (31.3); 2.493 (16.6); 2.370 (15.3); 2.328 (0.3); 2.001 (16.0); 1.221 (5.8); 1.202 (12.4); 1.184 (5.6); 0.008 (1.5); 0.000 (42.9); −0.008 (2.4)

Example 40: $^1$H-NMR(400.0 MHz, DMSO):
δ = 8.412 (8.2); 8.193 (4.1); 8.186 (4.2); 7.981 (3.7); 7.976 (3.8); 7.699 (1.7); 7.694 (1.7); 7.679 (2.3); 7.673 (2.3); 7.569 (3.1); 7.548 (2.3); 4.254 (0.9); 4.244 (0.4); 4.227 (1.0); 4.217 (1.3); 4.199 (0.4); 4.190 (1.3); 4.163 (0.4); 4.090 (0.4); 4.063 (1.2); 4.054 (0.4); 4.036 (1.4); 4.027 (0.9); 4.009 (0.5); 4.000 (0.9); 3.325 (44.5); 2.670 (0.4); 2.524 (1.3); 2.506 (50.5); 2.501 (65.8); 2.497 (48.8); 2.454 (16.0); 2.333 (0.3); 2.328 (0.4); 2.324 (0.3); 1.236 (0.4); 0.000 (5.1)

Example 41: $^1$H-NMR(400.0 MHz, DMSO):
δ = 8.739 (14.3); 8.316 (2.9); 8.262 (11.1); 8.243 (11.3); 8.228 (10.1); 8.205 (10.1); 7.839 (0.5); 7.814 (0.4); 7.195 (16.0); 5.756 (6.3); 4.361 (0.4); 4.340 (1.0); 4.305 (1.5); 4.279 (1.3); 4.179 (0.4); 4.154 (0.7); 4.128 (2.0); 4.101 (2.3); 4.092 (1.8); 4.074 (1.1); 4.064 (1.6); 4.038 (0.6); 3.845 (2.2); 3.324 (955.8); 2.675 (4.3); 2.671 (5.9); 2.666 (4.3); 2.662 (2.0); 2.524 (15.5); 2.511 (332.6); 2.506 (669.9); 2.502 (882.7); 2.497 (635.7); 2.493 (303.8); 2.337 (2.1); 2.333 (4.2); 2.328 (5.8); 2.324 (4.2); 2.086 (0.4); 1.257 (0.6); 1.235 (0.9); 1.215 (0.4); 1.183 (0.4); 1.166 (0.3); 0.146 (1.0); 0.008 (7.8); 0.000 (237.7); −0.009 (7.9); −0.150 (1.0)

TABLE 4-continued

NMR data of the compounds according to Table 1:

Example 43: $^1$H-NMR(400.0 MHz, DMSO):
δ = 8.342 (5.7); 7.626 (3.4); 7.622 (3.5); 7.404 (2.4); 7.384 (3.2); 7.277 (2.2); 7.273 (2.1); 7.257 (1.6); 7.253 (1.6); 6.336 (5.1); 4.117 (1.2); 4.091 (3.8); 4.066 (3.9); 4.040 (1.3); 3.326 (89.7); 2.671 (0.5); 2.560 (1.5); 2.541 (4.4); 2.522 (5.9); 2.506 (62.9); 2.502 (80.4); 2.497 (60.3); 2.389 (16.0); 2.333 (0.4); 2.328 (0.5); 1.212 (5.5); 1.193 (11.4); 1.174 (5.3); 0.000 (8.5)

Example 44: $^1$H-NMR(400.0 MHz, DMSO):
δ = 8.360 (5.0); 7.796 (2.9); 7.778 (2.9); 7.438 (2.5); 7.411 (2.5); 6.398 (4.4); 5.757 (1.7); 4.059 (1.2); 4.033 (3.9); 4.007 (4.1); 3.981 (1.4); 3.326 (68.0); 2.675 (0.4); 2.671 (0.6); 2.666 (0.4); 2.524 (1.4); 2.511 (32.7); 2.506 (66.0); 2.502 (87.1); 2.497 (64.1); 2.493 (31.8); 2.427 (16.0); 2.378 (0.4); 2.368 (0.6); 2.333 (0.5); 2.329 (0.6); 2.324 (0.5); 2.268 (14.5); 2.066 (0.4); 0.000 (5.8)

Example 45: $^1$H-NMR(400.0 MHz, DMSO):
δ = 8.550 (2.5); 8.532 (3.5); 7.854 (7.4); 7.460 (2.2); 7.437 (3.2); 6.766 (4.1); 6.760 (3.1); 4.292 (0.4); 4.265 (0.5); 4.255 (0.6); 4.228 (0.6); 4.155 (0.4); 4.137 (0.5); 4.128 (1.3); 4.102 (1.7); 4.076 (1.3); 4.068 (0.5); 4.049 (0.4); 4.040 (0.3); 3.986 (0.5); 3.960 (0.6); 3.950 (0.5); 3.923 (0.5); 3.328 (8.8); 2.505 (17.6); 2.501 (23.0); 2.497 (17.5); 2.428 (16.0); 2.144 (11.4); 2.136 (8.4); 2.086 (3.4); 2.002 (3.4); 1.954 (7.2); 1.951 (6.5); 1.906 (3.7); 1.903 (3.3); 0.000 (0.9)

Example 46: $^1$H-NMR(400.0 MHz, DMSO):
δ = 8.428 (5.0); 8.317 (0.4); 8.020 (3.1); 8.002 (3.1); 7.568 (2.4); 7.541 (2.3); 6.422 (4.5); 4.259 (0.5); 4.251 (0.3); 4.232 (0.6); 4.223 (0.8); 4.196 (0.8); 4.127 (1.0); 4.100 (1.4); 4.091 (0.7); 4.073 (0.8); 4.064 (0.6); 3.328 (131.6); 2.729 (0.5); 2.676 (0.8); 2.671 (1.2); 2.666 (0.9); 2.662 (0.4); 2.524 (2.8); 2.520 (4.2); 2.511 (60.6); 2.506 (125.9); 2.502 (168.1); 2.497 (123.8); 2.493 (61.0); 2.468 (16.0); 2.338 (0.4); 2.333 (0.9); 2.328 (1.6); 2.280 (14.4); 2.105 (0.4); 1.234 (0.4); 0.008 (1.2); 0.000 (41.0); −0.009 (1.5)

Example 47: $^1$H-NMR(400.0 MHz, DMSO):
δ = 8.642 (4.8); 7.721 (3.3); 7.716 (3.4); 7.444 (2.2); 7.424 (3.3); 7.357 (2.5); 7.352 (2.4); 7.337 (1.6); 7.332 (1.6); 7.100 (5.1); 4.098 (1.2); 4.073 (4.0); 4.047 (4.1); 4.021 (1.4); 3.324 (40.9); 2.671 (0.4); 2.524 (0.9); 2.519 (1.4); 2.511 (20.0); 2.506 (41.1); 2.502 (54.6); 2.497 (39.7); 2.492 (19.0); 2.400 (16.0); 2.333 (0.6); 2.328 (0.5); 2.324 (0.3); 0.008 (1.8); 0.000 (55.9); −0.009 (1.9)

Example 48: $^1$H-NMR(400.0 MHz, DMSO):
δ = 8.317 (0.7); 8.166 (5.0); 8.055 (0.5); 7.718 (5.2); 7.703 (3.7); 7.623 (0.4); 7.435 (2.6); 7.415 (3.6); 4.274 (0.6); 4.247 (0.6); 4.237 (0.7); 4.210 (0.7); 4.149 (1.0); 4.140 (0.4); 4.122 (3.0); 4.112 (0.5); 4.095 (3.1); 4.068 (1.1); 4.015 (0.7); 3.988 (0.8); 3.978 (0.6); 3.951 (0.6); 3.354 (1.2); 3.328 (188.4); 2.680 (0.7); 2.676 (1.1); 2.671 (1.4); 2.666 (1.1); 2.662 (0.6); 2.574 (0.3); 2.524 (3.6); 2.520 (5.5); 2.511 (74.3); 2.506 (152.5); 2.502 (202.5); 2.497 (147.9); 2.493 (71.9); 2.415 (14.9); 2.365 (1.2); 2.353 (0.8); 2.338 (0.5); 2.333 (1.1); 2.329 (1.5); 2.324 (1.2); 2.319 (0.9); 2.307 (12.9); 2.246 (1.2); 2.149 (0.8); 2.127 (0.3); 2.099 (15.7); 2.031 (0.4); 2.007 (16.0); 1.234 (0.6); 1.031 (0.4); 1.013 (0.7); 0.995 (0.3); 0.008 (1.5); 0.000 (51.5); −0.009 (1.7)

Example 49: $^1$H-NMR(400.0 MHz, DMSO):
δ = 8.638 (2.3); 8.621 (3.3); 8.317 (0.7); 7.918 (4.8); 7.465 (2.1); 7.439 (3.0); 7.132 (4.6); 4.301 (0.4); 4.273 (1.0); 4.263 (0.5); 4.236 (0.5); 4.167 (0.4); 4.140 (1.0); 4.130 (1.0); 4.104 (1.3); 4.082 (0.9); 4.055 (1.0); 4.046 (0.4); 4.028 (0.4); 4.019 (0.4); 3.946 (0.5); 3.919 (0.6); 3.909 (0.4); 3.883 (0.5); 3.325 (200.0); 2.675 (1.7); 2.671 (2.3); 2.666 (1.7); 2.524 (5.6); 2.506 (258.8); 2.502 (340.1); 2.497 (251.2); 2.428 (16.0); 2.333 (1.8); 2.328 (2.4); 2.324 (1.8); 2.153 (11.1); 2.146 (8.1); 0.146 (1.2); 0.008 (8.9); 0.000 (277.2); −0.008 (10.7); −0.150 (1.3)

Example 50: $^1$H-NMR(400.0 MHz, DMSO):
δ = 8.700 (5.0); 8.316 (0.5); 8.011 (3.7); 8.005 (3.9); 7.698 (1.8); 7.692 (1.7); 7.677 (2.4); 7.672 (2.4); 7.570 (3.1); 7.549 (2.3); 7.114 (5.2); 5.756 (0.7); 4.259 (0.9); 4.249 (0.4); 4.232 (1.0); 4.222 (1.3); 4.205 (0.4); 4.195 (1.3); 4.168 (0.4); 4.059 (0.3); 4.031 (1.2); 4.022 (0.4); 4.004 (1.3); 3.995 (1.0); 3.977 (0.5); 3.968 (1.0); 3.941 (0.3); 3.324 (164.1); 2.732 (0.6); 2.675 (0.9); 2.671 (1.2); 2.666 (0.9); 2.524 (13.5); 2.510 (69.4); 2.506 (137.1); 2.501 (179.6); 2.497 (130.3); 2.493 (62.9); 2.455 (16.0); 2.427 (0.4); 2.333 (0.9); 2.328 (1.2); 2.324 (0.9); 2.301 (0.4); 0.008 (1.8); 0.000 (44.1); −0.009 (1.4)

Example 51: $^1$H-NMR(400.0 MHz, DMSO):
δ = 8.490 (4.8); 7.990 (0.4); 7.607 (5.7); 7.385 (0.3); 7.320 (4.5); 6.753 (5.3); 5.756 (0.5); 4.049 (1.2); 4.024 (3.9); 3.998 (4.0); 3.972 (1.4); 3.330 (31.0); 2.524 (0.5); 2.519 (0.8); 2.511 (11.0); 2.506 (22.7); 2.502 (30.0); 2.497 (22.2); 2.493 (11.1); 2.376 (15.2); 2.347 (0.6); 2.338 (1.2); 2.329 (0.4); 2.145 (1.1); 2.055 (0.5); 2.027 (16.0); 2.002 (4.3); 1.954 (9.8); 1.906 (4.9); 0.987 (0.5); 0.969 (0.7); 0.008 (1.7); 0.000 (48.0); −0.009 (2.0)

Example 52: $^1$H-NMR(400.0 MHz, DMSO):
δ = 8.460 (4.2); 8.038 (2.4); 8.020 (2.4); 7.570 (1.9); 7.543 (1.9); 6.370 (4.5); 5.756 (15.0); 4.262 (0.4); 4.234 (0.5); 4.225 (0.7); 4.198 (0.6); 4.131 (0.7); 4.104 (0.8); 4.095 (0.5); 4.068 (0.5); 3.330 (14.1); 2.827 (0.4); 2.810 (1.0); 2.793 (1.4); 2.776 (1.0); 2.759 (0.4); 2.524 (2.2); 2.511 (7.2); 2.507 (14.2); 2.502 (18.4); 2.498 (13.7); 2.472 (11.8); 1.216 (16.0); 1.199 (15.6); 0.000 (4.0)

Example 53: $^1$H-NMR(400.0 MHz, DMSO):
δ = 8.714 (3.0); 8.680 (4.0); 8.316 (0.7); 8.194 (9.3); 7.845 (3.3); 7.819 (4.4); 7.195 (4.5); 7.189 (3.5); 5.756 (0.3); 4.401 (0.6); 4.374 (0.7); 4.364 (0.7); 4.337 (0.8); 4.246 (0.7); 4.237 (0.8); 4.219 (0.9); 4.210 (1.1); 4.191 (0.4); 4.183 (1.1); 4.156 (0.4); 4.071 (1.0); 4.044 (1.1); 4.035 (0.8); 4.018 (0.6); 4.008 (0.8); 3.992 (0.7); 3.981 (0.5); 3.966 (0.8); 3.955 (0.7); 3.939 (0.3); 3.929 (0.7); 3.324 (258.8); 2.739 (0.3); 2.675 (1.2); 2.671 (1.6); 2.666 (1.2); 2.524 (4.5); 2.510 (90.1); 2.506 (181.6); 2.502 (240.3); 2.497 (174.5); 2.493 (84.2); 2.469 (16.0); 2.333 (1.7); 2.328 (2.0); 2.324 (1.3); 0.146 (1.5); 0.008 (12.7); 0.000 (335.6); −0.009 (12.4); −0.027 (0.4); −0.150 (1.5)

Example 54: $^1$H-NMR(400.0 MHz, DMSO):
δ = 8.663 (15.1); 8.316 (1.6); 7.888 (10.5); 7.882 (10.6); 7.732 (13.1); 7.711 (15.4); 7.479 (8.1); 7.474 (7.8); 7.458 (6.9); 7.452 (6.8); 7.137 (16.0); 4.221 (3.5); 4.196 (11.1); 4.170 (11.5); 4.145 (3.9); 3.324 (386.1); 2.675 (2.6); 2.671 (3.5); 2.666 (2.6); 2.524 (9.9); 2.510 (197.9); 2.506 (393.6); 2.502 (514.9); 2.497 (372.2); 2.493 (178.9); 2.333 (2.5); 2.328 (3.3); 2.324 (2.4); 0.146 (1.8); 0.008 (15.3); 0.000 (403.7); −0.009 (14.3); −0.150 (1.7)

TABLE 4-continued

NMR data of the compounds according to Table 1:

Example 55: $^1$H-NMR(400.0 MHz, DMSO):
δ = 8.668 (4.7); 8.315 (0.4); 8.147 (3.0); 8.128 (3.1); 7.598 (2.2); 7.571 (2.2); 6.986 (1.3); 6.852 (5.3); 6.716 (1.6); 5.756 (0.3); 4.275 (0.4); 4.249 (0.5); 4.240 (0.6); 4.213 (0.6); 4.092 (0.6); 4.065 (0.7); 4.056 (0.6); 4.038 (0.3); 4.029 (0.5); 3.323 (140.2); 2.740 (0.5); 2.679 (0.4); 2.675 (0.7); 2.671 (1.0); 2.666 (0.8); 2.661 (0.4); 2.524 (2.4); 2.519 (3.7); 2.510 (55.7); 2.506 (116.1); 2.501 (156.5); 2.497 (114.8); 2.492 (56.5); 2.478 (16.0); 2.333 (0.9); 2.328 (1.1); 2.324 (0.8); 2.319 (0.4); 0.000 (0.4)
Example 56: $^1$H-NMR(400.0 MHz, DMSO):
δ = 8.638 (2.4); 8.621 (3.4); 7.918 (5.0); 7.464 (2.1); 7.439 (3.1); 7.131 (4.8); 4.300 (0.4); 4.273 (0.5); 4.263 (0.6); 4.236 (0.6); 4.167 (0.4); 4.157 (0.3); 4.140 (0.5); 4.130 (1.0); 4.103 (1.1); 4.082 (1.0); 4.055 (1.1); 4.045 (0.5); 4.028 (0.4); 4.018 (0.5); 3.945 (0.5); 3.918 (0.6); 3.909 (0.5); 3.882 (0.5); 3.325 (56.3); 2.675 (0.5); 2.671 (0.7); 2.666 (0.5); 2.524 (1.8); 2.510 (37.0); 2.506 (72.9); 2.502 (95.9); 2.497 (71.3); 2.493 (35.6); 2.428 (16.0); 2.333 (0.5); 2.328 (0.7); 2.324 (0.5); 2.153 (11.5); 2.145 (8.4); 0.146 (0.4); 0.008 (3.1); 0.000 (80.1); −0.008 (3.4); −0.150 (0.4)
Example 57: $^1$H-NMR(400.0 MHz, DMSO):
δ = 8.382 (5.0); 7.806 (2.9); 7.788 (2.9); 7.438 (2.5); 7.411 (2.5); 6.368 (4.5); 6.366 (4.6); 5.756 (1.5); 4.066 (1.2); 4.041 (3.9); 4.015 (4.1); 3.989 (1.4); 3.324 (45.7); 2.675 (0.4); 2.671 (0.5); 2.666 (0.4); 2.574 (1.3); 2.555 (4.0); 2.536 (4.2); 2.510 (27.3); 2.506 (54.9); 2.502 (73.2); 2.497 (55.5); 2.493 (29.3); 2.426 (16.0); 2.333 (0.4); 2.328 (0.5); 2.324 (0.4); 1.213 (5.8); 1.195 (12.3); 1.176 (5.7); 0.008 (1.9); 0.000 (50.4); −0.009 (2.8)
Example 58: $^1$H-NMR(400.0 MHz, DMSO):
δ = 8.581 (5.7); 8.316 (0.5); 8.155 (0.4); 8.146 (2.6); 8.141 (3.2); 8.133 (3.0); 8.122 (3.0); 7.889 (2.9); 7.871 (2.9); 7.555 (0.9); 7.546 (6.6); 7.540 (6.3); 7.532 (3.9); 7.529 (4.1); 7.519 (1.1); 7.505 (0.4); 7.473 (2.6); 7.447 (2.6); 7.132 (6.0); 5.756 (0.9); 4.079 (1.2); 4.053 (3.8); 4.027 (4.0); 4.001 (1.4); 3.324 (139.4); 2.675 (0.8); 2.671 (1.2); 2.666 (0.9); 2.506 (133.0); 2.502 (176.5); 2.497 (131.1); 2.446 (16.0); 2.401 (0.4); 2.333 (0.9); 2.328 (1.2); 2.324 (1.0); 0.146 (1.0); 0.008 (8.0); 0.000 (207.3); −0.008 (8.4); −0.150 (1.0)
Example 59: $^1$H-NMR(400.0 MHz, DMSO):
δ = 8.691 (4.6); 8.316 (0.3); 7.917 (6.2); 7.676 (5.2); 7.203 (5.0); 5.756 (0.6); 4.116 (0.8); 4.112 (0.8); 4.104 (0.3); 4.090 (2.3); 4.087 (2.3); 4.065 (2.3); 4.061 (2.3); 4.039 (0.8); 4.035 (0.8); 3.324 (85.4); 2.675 (0.6); 2.671 (0.8); 2.666 (0.6); 2.524 (2.2); 2.511 (43.3); 2.506 (85.9); 2.502 (112.3); 2.497 (81.1); 2.493 (38.9); 2.406 (16.0); 2.364 (0.6); 2.333 (0.5); 2.328 (0.7); 2.324 (0.5); 0.146 (0.4); 0.008 (3.1); 0.000 (86.6); −0.009 (3.2); −0.150 (0.4)

Use Examples

1. *Boophilus microplus*—Injection Test
Solvent: dimethyl sulphoxide

To produce an appropriate active compound formulation, 10 mg of active compound are mixed with 0.5 ml of solvent and the concentrate is diluted with solvent to the desired concentration.

1 μl of the active compound solution is injected into the abdomen of 5 engorged adult female cattle ticks (*Boophilus microplus*). The animals are transferred into dishes and kept in a climate-controlled room.

The efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples showed an efficacy of 100% at an application rate of 20 μg/animal: 2, 4, 5, 6, 9, 22, 26, 34, 47, 50, 53, 59

2. *Meloidogyne Incognita* Test
Solvent: 125.0 parts by weight of acetone

To produce an appropriate active compound formulation, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples showed an efficacy of 100% at an application rate of 20 ppm: 18, 21, 33, 45, 55

In this test, for example, the following compounds from the preparation examples showed an efficacy of 90% at an application rate of 20 ppm: 9, 12, 18, 21, 26, 27, 30, 41, 55

3. *Phaedon cochleariae*—Spray Test
Solvent: 78.0 parts by weight of acetone
1.5 parts by weight of dimethylformamide
Emulsifier: alkylaryl polyglycol ether To produce an appropriate active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound formulation of the desired concentration and, after drying, populated with larvae of the mustard beetle (*Phaedon cochleariae*).

After 7 days, the efficacy in % is determined 100% means that all the beetle larvae have been killed; 0% means that no beetle larvae have been killed.

In this test, for example, the following compound from the preparation examples showed an efficacy of 100% at an application rate of 500 g/ha: 2, 9, 44, 53, 55

In this test, for example, the following compounds of the preparation examples showed an efficacy of 83% at an application rate of 500 g/ha: 18, 34, 46

4. *Tetranychus urticae*—Spray Test, OP-Resistant
Solvent: 78.0 parts by weight of acetone
 1.5 parts by weight of dimethylformamide
Emulsifier: alkylaryl polyglycol ether To produce an appropriate active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active compound formulation of the desired concentration.

After 6 days, the efficacy in % is determined. 100% means that all the spider mites have been killed; 0% means that none of the spider mites have been killed.

In this test, for example, the following compounds of the Preparation Examples showed an efficacy of 100% at an application rate of 500 g/ha: 1, 2, 4, 5, 6, 7, 8, 9, 10, 13, 14, 15, 16, 17, 18, 19, 20, 22, 23, 26, 29, 30, 31, 32, 33, 34, 36, 37, 39, 40, 41, 44, 45, 46, 47, 50, 51, 52, 53, 54, 55, 57, 59

In this test, for example, the following compounds of the Preparation Examples showed an efficacy of 90% at an application rate of 500 g/ha: 12, 24, 28, 35, 43, 48

5. *Meloidogyne incognita* Test
Solvent: 7 parts by weight of dimethylformamide
Emulsifier: 2.5 parts by weight of alkylaryl poly glycol ether To produce an appropriate active compound formulation, 1 part by weight of active compound is mixed with the stated amounts of solvent and emulsifier, and the concentrate is diluted with water to the desired concentration, it being necessary to include the volume of soil which is drenched in the calculation. It should be ensured that a concentration of 20 ppm of emulsifier in the soil is not exceeded. To produce further test concentrations, water is used for dilution.

Pots filled with soil (loamy sand) are watered with the active compound solution. An egg/larvae suspension of the southern root-knot nematode (*Meloidogyne incognita*) is added, lettuce seeds are scattered over the surface of the soil, and they are covered over with quartz sand. The lettuce seeds germinate and the plants develop. The galls develop on the roots.

After 21 days, the nematicidal efficacy in % is determined by the formation of galls. 100% means that no galls have been found; 0% means that the number of galls on the treated plants corresponds to the untreated control.

In this test, for example, the following compounds of the Preparation Examples showed an efficacy of 85% at an application rate of 8 ppm: 2

6. *Tetranychus urticae*—Spray Test, OP-Resistant
Solvent: 7 parts by weight of dimethylformamide
Emulsifier: alkylaryl polyglycol ether To produce an appropriate active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bean plants (*Phaseolus vulgaris*) heavily infested by all stages of the greenhouse red spider mite (*Tetranychus urticae*) are treated by spraying with the active compound formulation in the desired concentration.

After 7 days, the efficacy in % is determined. 100% means that all the spider mites have been killed; 0% means that none of the spider mites have been killed.

In this test, for example, the following compounds from the preparation examples showed an efficacy of 100% at an application rate of 20 ppm: 49, 56

Comparative Examples

1. *Phaedon cochleariae*—Spray Test (PHAECO)

Solvent: 78.0 parts by weight of acetone
 1.5 parts by weight of dimethylformamide
Emulsifier: alkylaryl polyglycol ether To produce an appropriate active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound formulation of the desired concentration and, after drying, populated with larvae of the mustard beetle (*Phaedon cochleariae*).

After the desired period of time, the effect in % is determined. 100% means that all the beetle larvae have been killed; 0% means that no beetle larvae have been killed.

In this test, for example, the following compounds of the Preparation Examples showed superior efficacy compared to 4-[6-oxo-4-(trifluoromethyl)pyrimidin-1-yl]-2-(2,2,2-trifluoroethylsulphinyl)benzonitrile and 5-fluoro-4-[6-oxo-4-(trifluoromethyl)pyrimidin-1-yl]-2-(2,2,2-trifluoroethylsulphinyl)benzonitrile: see Table 5 below.

2. *Tetranychus urticae*—Spray Test; OP-Resistant (TETHER)

Solvent: 78.0 parts by weight of acetone
 1.5 parts by weight of dimethylformamide
Emulsifier: alkylaryl polyglycol ether To produce an appropriate active compound formulation, 1 part by weight of active compound is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active compound formulation of the desired concentration.

After the desired period of time, the effect in % is determined 100% means that all the spider mites have been killed; 0% means that none of the spider mites have been killed.

In this test, for example, the following compounds of the Preparation Examples showed superior efficacy compared to 4-[6-oxo-4-(trifluoromethyl)pyrimidin-1-yl]-2-(2,2,2-trifluoroethylsulphinyl)benzonitrile and 5-fluoro-4-[6-oxo-4-(trifluoromethyl)pyrimidin-1-yl]-2-(2,2,2-trifluoroethylsulphinyl)benzonitrile: see Table 5 below.

TABLE 5

| Substance | Structure | Animal species | Concentration | % mortality | dat |
|---|---|---|---|---|---|
| 4-[6-oxo-4-(trifluoromethyl)pyrimidin-1-yl]-2-(2,2,2-trifluoroethylsulphinyl)benzonitrile | (structure) | PHAECO<br>TETRUR | 500 g/ha<br>20 g/ha | 0<br>0 | 7 dat<br>6 dat |
| Example 2 according to the invention | (structure) | PHAECO | 500 g/ha | 100 | 7 dat |
| Example 6 according to the invention | (structure) | TETRUR | 20 g/ha | 100 | 6 dat |
| 5-fluoro-4-[6-oxo-4-(trifluoromethyl) pyrimidin-1-yl]-2-(2,2,2-trifluoroethylsulphinyl)benzonitrile | (structure) | PHAECO | 500 g/ha | 50 | 7 dat |

The invention claimed is:

1. Compound of the formula (I),

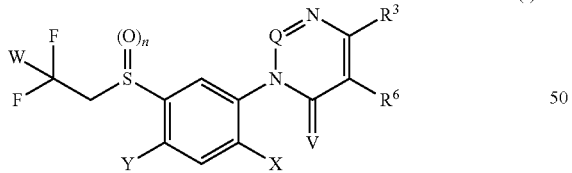

(I)

in which

V represents oxygen;
Q represents C—$R^5$, where
  $R^5$ represents hydrogen, halogen, amino, cyano, nitro, ($C_1$-$C_6$)-alkyl, ($C_1$-$C_6$)-haloalkyl, ($C_1$-$C_6$)-alkylsulphanyl, ($C_1$-$C_6$)-alkylsulphinyl, ($C_1$-$C_6$)-alkylsulphonyl, ($C_1$-$C_6$)-haloalkylsulphanyl, ($C_1$-$C_6$)-haloalkylsulphinyl, ($C_1$-$C_6$)-haloalkylsulphonyl, ($C_3$-$C_6$)-cycloalkyl or ($C_1$-$C_6$)-alkoxy;
$R^3$ and $R^6$ independently of one another
represent hydrogen, halogen, cyano or nitro; or
  represent ($C_1$-$C_6$)-alkyl, ($C_1$-$C_6$)-haloalkyl, ($C_2$-$C_6$)-alkenyl, ($C_2$-$C_6$)-alkynyl, ($C_1$-$C_6$)-alkoxy, ($C_1$-$C_6$)-haloalkoxy, ($C_1$-$C_6$)-haloalkylsulphanyl, ($C_1$-$C_6$)-haloalkylsulphinyl, ($C_1$-$C_6$)-haloalkylsulphonyl, ($C_1$-$C_6$)-alkylsulphanyl, ($C_1$-$C_6$)-alkylsulphinyl, ($C_1$-$C_6$)-alkylsulphonyl, ($C_1$-$C_5$)-alkylcarbonyl, ($C_1$-$C_5$)-haloalkylcarbonyl or ($C_2$-$C_6$)-alkoxycarbonyl; or
  represent ($C_3$-$C_6$)-cycloalkyl, ($C_3$-$C_6$)-cycloalkyl-($C_1$-$C_3$)-alkyl or ($C_3$-$C_6$)-cycloalkenyl, where the radicals mentioned above may optionally be substituted by halogen, alkyl, cyano, nitro, alkoxy, haloalkyl or haloalkoxy; or
  represent phenyl, heteroaryl, phenyl-($C_1$-$C_3$)-alkyl or heteroaryl-($C_1$-$C_3$)-alkyl, where the radicals mentioned above may optionally be substituted by halogen, alkyl, cyano, nitro, alkoxy, haloalkyl or haloalkoxy; or
  represent NR'R",
  where R' and R" independently of one another represent hydrogen, cyano, ($C_1$-$C_4$)-alkyl, ($C_1$-$C_4$)-haloalkyl, ($C_1$-$C_4$)-cyanoalkyl, ($C_1$-$C_4$)-hydroxyalkyl, ($C_1$-$C_4$)-alkoxy-($C_1$-$C_4$)-alkyl, ($C_1$-$C_4$)-alkylsulphanyl-($C_1$-$C_4$)-alkyl, ($C_1$-$C_4$)-alkylsulphinyl-($C_1$-$C_4$)-alkyl, ($C_1$-$C_4$)-alkylsulphonyl-($C_1$-$C_4$)-alkyl, ($C_3$-$C_4$)-alkenyl, ($C_3$-$C_4$)-haloalkenyl, ($C_2$-$C_4$)-cyanoalkenyl, ($C_3$-$C_4$)-alkynyl, ($C_3$-$C_4$)- haloalkynyl, $(C_3-C_4)$-cyanoalkynyl, $(C_1-C_4)$-alkylcarbonyl or $(C_1-C_4)$-alkoxycarbonyl;
or
where R' and R" together with the nitrogen atom to which they are attached may form an optionally halogen-, alkyl-, cyano-, nitro-, alkoxy-, haloalkyl- or haloalkoxy-substituted, saturated or unsaturated three- to eight-membered ring optionally interrupted by one or more heteroatoms independently selected from the group consisting of O, S and N, with the proviso that two oxygen atoms must not be directly adjacent to one another; or W represents hydrogen or halogen;

n represents the number 0 or 1;

Y represents halogen, $(C_1-C_4)$-alkyl, $(C_1-C_4)$-alkoxy, $(C_1-C_4)$-haloalkoxy or amino; or
represents NR'''R'''',
where R''' and R'''' independently of one another represent hydrogen, $(C_1-C_4)$-alkyl or $(C_2-C_4)$-haloalkyl;

X represents halogen, cyano, $(C_1-C_4)$-alkyl, $(C_1-C_4)$-haloalkyl or $(C_1-C_4)$-alkoxy.

2. Compound according to claim 1, in which
Q represents C—$R^5$, where
$R^5$ represents hydrogen, halogen, amino, cyano, nitro, $(C_1-C_4)$-alkyl, $(C_1-C_4)$-haloalkyl, $(C_3-C_6)$-cycloalkyl or $(C_1-C_4)$-alkoxy;
$R^3$ and $R^6$ independently of one another
represent hydrogen or halogen; or
represent $(C_1-C_4)$-alkyl, $(C_1-C_4)$-haloalkyl, $(C_1-C_4)$-alkoxy or $(C_1-C_4)$-haloalkoxy; or
represent $(C_3-C_6)$-cycloalkyl or $(C_3-C_6)$-cycloalkyl-$(C_1-C_2)$-alkyl, where the radicals mentioned above may optionally be substituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or
represent phenyl or phenyl-$(C_1-C_3)$-alkyl, where the radicals mentioned above may optionally be mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or
represent heteroaryl selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, indolyl, isoindolyl and indazolyl, where the radicals mentioned above may optionally be mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy; or
represent NR'R",
where R' and R" independently of one another represent hydrogen, $(C_1-C_4)$-alkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-alkylsulphanyl-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl, $(C_1-C_4)$-alkylcarbonyl or $(C_1-C_4)$-alkoxycarbonyl;
or
where R' and R" together with the nitrogen atom to which they are attached may form a saturated four- to six-membered ring which is optionally mono- or disubstituted by fluorine, chlorine, bromine, iodine, $(C_1-C_3)$-alkyl, cyano, nitro, $(C_1-C_3)$-alkoxy, $(C_1-C_3)$-haloalkyl or $(C_1-C_3)$-haloalkoxy and optionally interrupted by a heteroatom selected from the group consisting of O, S and N;

W represents hydrogen or fluorine;

Y represents fluorine, chlorine, bromine, methyl, ethyl, methoxy, ethoxy, difluoromethoxy, trifluoromethoxy, amino, methylamino or dimethylamino;

X represents fluorine, chlorine, bromine, cyano, methyl, ethyl, trifluoromethyl, methoxy or ethoxy.

3. Compound according to claim 1, in which
Q represents C—$R^5$, where
$R^5$ represents hydrogen, methyl, ethyl, methoxy, cyclopropyl or trifluoromethyl;
$R^3$ and $R^6$ independently of one another represent hydrogen, fluorine, methyl, ethyl, isopropyl, trifluoromethyl, pentafluoroethyl, difluoromethyl, 1,1-difluoroethyl, difluorochloromethyl, cyclopropyl or phenyl;

W represents hydrogen or fluorine;

Y represents fluorine, chlorine, bromine, methyl, or methoxy;

X represents chlorine, fluorine or methyl.

4. Compound according to claim 1, in which
Q represents C—$R^5$, where
$R^5$ represents hydrogen or methyl;
$R^3$ represents hydrogen, methyl, ethyl, cyclopropyl, isopropyl, difluoromethyl, trifluoromethyl, pentafluoroethyl, 1,1-difluoroethyl or phenyl;
$R^6$ represents hydrogen, fluorine or methyl;

W represents fluorine;

Y represents bromine, chlorine or methyl;

X represents chlorine, fluorine or methyl.

5. Formulation, comprising at least one compound of the formula (I) according to claim 1.

6. Formulation according to claim 5, further comprising at least one extender and/or at least one surface-active substance.

7. Formulation according to claim 5, wherein the compound of the formula (I) is in a mixture with at least one further active compound.

8. Method for controlling one or more pests, comprising allowing a compound of the formula (I) according to claim 1 to act on the pests and/or a habitat thereof, wherein the pests are selected from the group consisting of ticks, spider mites, beetles and southern root-knot nematodes.

9. Method for protecting seed or a germinating plant from pests, comprising contacting seed with a compound of the formula (I) according to claim 1, wherein the pests are selected from the group consisting of ticks, spider mites, beetles and southern root-knot nematodes.

10. Seed obtained by a method according to claim 9.

11. Compound according to claim 1, in which
Q represents C—$R^5$, where
$R^5$ represents hydrogen, methyl, ethyl, methoxy, cyclopropyl or trifluoromethyl;
$R^3$ and $R^6$ independently of one another represent hydrogen, fluorine, methyl, ethyl, isopropyl, trifluoromethyl, pentafluoroethyl, difluoromethyl, 1,1-difluoroethyl, difluorochloromethyl, cyclopropyl or phenyl;

W represents hydrogen or fluorine;

X and Y represent a combination (Y,X) selected from the group consisting of (Me,F), (Me,Cl), (Me,Me), (Cl,Cl), (Cl,F), (MeO,F), (Br,F), and (F,F).

12. Compound according to claim 1, in which

Q represents C—$R^5$, where $R^5$ represents hydrogen or methyl;

$R^3$ represents hydrogen, methyl, ethyl, cyclopropyl, isopropyl, difluoromethyl, trifluoromethyl, pentafluoroethyl, 1,1-difluoroethyl or phenyl;

$R^6$ represents hydrogen, fluorine or methyl;

W represents fluorine;

X and Y represent a combination (Y,X) selected from the group consisting of (Me,Cl), (Me,F), (Me,Me), (Cl,Cl), (Cl,F), and (Br,F).

13. Method according to claim 8, wherein the compound of formula (I) is applied to crops and/or a habitat thereof.

14. Method according to claim 8, wherein the compound of formula (I) is administered to an animal.

15. Compound according to claim 1, wherein $R^5$ represents halogen, amino, cyano, nitro, $(C_1$-$C_6)$-alkyl, $(C_1$-$C_6)$-haloalkyl, $(C_1$-$C_6)$-alkylsulphanyl, $(C_1$-$C_6)$-alkylsulphinyl, $(C_1$-$C_6)$-alkylsulphonyl, $(C_1$-$C_6)$-haloalkylsulphanyl, $(C_1$-$C_6)$-haloalkylsulphinyl, $(C_1$-$C_6)$-haloalkylsulphonyl, $(C_3$-$C_6)$-cycloalkyl or $(C_1$-$C_6)$-alkoxy.

\* \* \* \* \*